United States Patent [19]
Akasaki et al.

[11] Patent Number: 5,102,757
[45] Date of Patent: Apr. 7, 1992

[54] ELECTROPHOTOGRAPHIC PHOTOSENSITIVE MEMBER AND IMAGE FORMING PROCESS

[75] Inventors: Yutaka Akasaki; Hidekazu Aonuma; Kazuya Hongo; Katsuhiro Sato; Katsumi Nukada; Teruumi Marumo, all of Kanagawa, Japan

[73] Assignee: Fuji Xerox Co., Ltd., Tokyo, Japan

[21] Appl. No.: 742,105

[22] Filed: Aug. 5, 1991

[30] Foreign Application Priority Data

| Sep. 13, 1988 | [JP] | Japan | 63-227493 |
| Oct. 5, 1988 | [JP] | Japan | 63-249734 |
| Oct. 5, 1988 | [JP] | Japan | 63-249735 |
| Oct. 15, 1988 | [JP] | Japan | 63-249738 |

[51] Int. Cl.$^5$ .......................... G03G 5/09; G03G 5/047; G03G 13/22
[52] U.S. Cl. .......................... 430/58; 430/59; 430/100; 430/126
[58] Field of Search .......................... 430/58, 59, 100

[56] References Cited

U.S. PATENT DOCUMENTS 3,877,935 4/1975 Regensburger et al. .......... 430/58
4,390,609 6/1983 Wiedemann .......... 430/67 X
4,882,254 11/1989 Loutfy et al. .......... 430/59

FOREIGN PATENT DOCUMENTS 47-26905 7/1972 Japan .......... 430/100

*Primary Examiner*—Roland Martin
*Attorney, Agent, or Firm*—Finnegan, Henderson, Farabow, Garrett and Dunner

[57] ABSTRACT

An electrophotographic photosensitive member has a charge-generating layer which includes selected photosensitive pigment particles and a compound which is a tetracyanoanthraquinodimethane compound, an anthraquinone compound, a dicyanovinyl compound, or a special quinone compound. The compound is incorporated in an amount in a range from 0.01 to 2 molar equivalents, preferably 0.1 to 1 molar equivalent, to the pigment, which has a positive hole transporting property. The photosensitive member has a charge-transporting layer and can also have a protective layer. The pigment is a phthalocyanine series pigment, a squearyrium series pigment, or a perylene series pigment. A process of using the photosensitive member includes reversal development and multicolor toner transfer. It is found that the process is adaptable to change in size of the transfer medium.

11 Claims, 4 Drawing Sheets

ELECTROPHOTOGRAPHIC PHOTOSENSITIVE MEMBER AND IMAGE FORMING PROCESS

FIELD OF THE INVENTION

This invention relates to an electrophotographic photosensitive member and an image-forming process using it. More particularly, the invention relates to an electrophotographic photosensitive member having a charge generating layer and a charge transporting layer successively formed on a conductive support.

BACKGROUND OF THE INVENTION

Electrophotographic photosensitive members using an inorganic photoconductive material such as selenium, a selenium alloy, zinc oxide, cadmium sulfide, etc., have been mainly used in the past. However, the electrophotoconductive photosensitive members using inorganic photoconductive materials have problems in the points of producibility, production cost, flexibility, etc.

Recently, for solving such problems, organic photoconductive materials have been vigorously pursued; and electrophotographic photosensitive members using a charge-transfer complex composed of polyvinyl carbazole and 2,4,7-trinitrofluorenone and electrophotographic photosensitive members using an eutectic complex of a pyryrium salt and alkylidenediarylene are known.

Also, most recently, an electrophotographic photosensitive member wherein a function of generating a charge by absorbing light and a function of transporting the charge thus generated are allocated to separate materials is proposed. For example, a double layer or multilayer type electrophotographic photoconductive member separately containing a bisazo pigment and a pyrazoline derivative in these layers in proposed as described in JP-A-58-16247 (the term "JP-A" as used herein means an "unexamined published Japanese patent application").

Furthermore, recently, it is proposed to prevent the increase of a residual potential by incorporating a cyanovinyl compound in a charge transporting layer together with an electron donative charge transfer material as described in JP-A-58-7643.

However, the electrophotographic photosensitive members using these organic photoconductive materials have low photosensitivity and are yet insufficient as photosensitive members. Also, the double layer or multilayer type electrophotographic photosensitive member wherein functions are allocated to a charge generating layer and a charge transporting layer having sufficiently satisfactory characteristics for practical use has not yet been obtained.

That is, in the double layer type electrophotographic photosensitive member having a charge generating layer and a charge transporting layer successively formed on a support, the photosensitivity is insufficient; and there are problems that the photosensitivity and the charging potential are largely changed by changes in the environmental conditions and also the potential cycle changes in the light-exposed portions whenever unexposed portions are large.

These problems are also seen in an ordinary process of transferring toner images formed by tonerdeveloping non-exposed portions on a photosensitive member onto a transfer material such as a paper but are particularly remarkable in an image-forming process including the steps of uniformly negatively charging a photosensitive member, forming electrostatic latent images by exposing the member to image-bearing radiation, forming toner images by development, and applying thereto a positive charge at the transfer of the toner images. That is, since the potentials at the exposed portions and the unexposed portions of the aforesaid photosensitive member greatly changes during a cycle, the density of the transferred images greatly differs between the initial images and images after making many copies. Also, when after making many copies, transfer papers are changed into transfer papers having a large size, the transfer density at the portions of the large transfer paper corresponding to the widened portions becomes higher or fog is formed at the portions.

SUMMARY OF THE INVENTION

The present invention has been made in consideration of the aforesaid circumstances and the object of this invention is to solve the aforesaid problems in conventional techniques.

That is, the object of this invention is to provide an electrophotographic photosensitive member showing good chargeability and having a high photosensitivity, the photosensitivity and the charged potential thereof being stable during changes of surrounding (environmental) conditions and the potentials at the exposed portions and the unexposed portions being stable at making many copies.

Another object of this invention is to provide an electrophotographic photosensitive member which is suitable for use in an image-forming process including the steps of uniformly charging an electrophotographic photosensitive member, after forming electrostatic latent images, attaching negatively charged toners to the low potential portions of the electrostatic latent images to form toner images, and transferring the toner images by applying a charge of a definite polarity.

Still another object of this invention is to provide an electrophotographic image-forming process capable of providing images having a uniform image density without causing large cycle change of potentials in exposed portions and unexposed portions, in the case of an electrophotographic process including the steps of uniformly negatively charging an electrophotographic photosensitive member, thereafter forming electrostatic latent images, attaching negatively charged toners to low potential portions of the electrostatic latent images to form toner images, and transferring the toner images by applying a charge of a definite polarity.

It has now been discovered that the aforesaid objects of this invention can be attained by using an electrophotographic photosensitive member having a charge generating layer and a charge transporting layer successively formed on a support, wherein the charge generating layer contains a charge generating pigment having a positive hole transporting property and at least one of the compounds represented by formula (Ia), (Ib), (Ic), and (Id) shown below in the binder resin thereof.

That is, the invention provides an electrophotographic photosensitive member having a charge generating layer and a charge transporting layer successively formed on a support, wherein the charge generating layer contains a charge generating pigment having a positive hole transporting property and at least one of a tetracyanoanthraquinodimethane compound represented by formula (Ia) shown below, an anthraquinone compound represented by formula (Ib) shown below, a dicyanovinyl compound represented by formula (Ic) shown below, and a quinone compound represented by formula (Id) shown below, in the binder resin thereof;

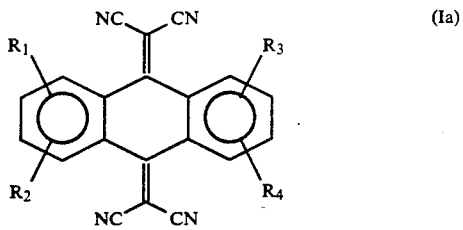

wherein $R_1$, $R_2$, $R_3$, and $R_4$ each represents a hydrogen atom, an alkyl group, an alkoxycarbonyl group, a halogen atom, an alkyl-substituted amino group, a hydroxy group, an aryl group, a nitro group, a cyano group, a carboxyalkyl group, an aralkyl group, an alkoxy group, an aryloxy group, an aralkyloxy group, a carboxyaryl group, a carboxyaralkyl group, an aryloxycarbonyl group, or an aralkyloxycarbonyl group;

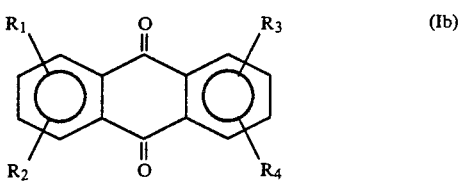

wherein $R_1$, $R_2$, $R_3$, and $R_4$ are as defined above for the compound of formula (Ia);

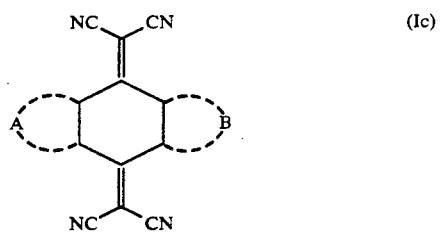

wherein A and B each represents a group forming a ring selected from those shown by formulae (1), (2), and (3) below, at least one of A and B representing a group forming a ring shown by formula (1) or (2);

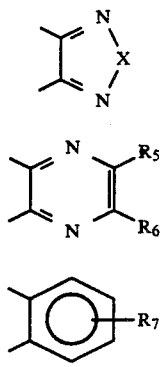

wherein X represents a selenium atom or a sulfur atom; $R_5$ and $R_6$ each represents a hydrogen atom, an alkyl group, an aryl group, an alkoxycarbonyl group, or an arylcarbonyl group; and $R_7$ represents a hydrogen atom, an alkyl group, a halogen atom, an aryl group, an alkoxy group, an aryloxy group, an alkoxycarbonyl group, an arylcarbonyl group, a nitro group, a cyano group, or a benzyloxy group; and

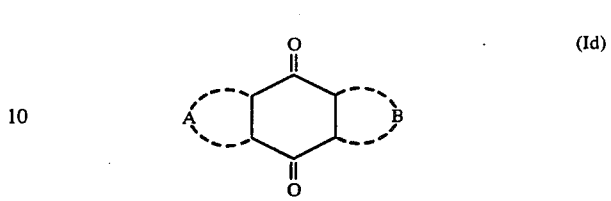

wherein A and B are as defined above for the compound of formula (Ic).

In the formulas (Ia) to (Id), the alkyl group, the alkoxy group, and the alkyl moiety of the aralkyl group each has 1 to 20 carbon atoms. The term "aryl group" used herein means an unsubstituted or substituted phenyl group or an unsubstituted or substituted naphthyl group.

DETAILED DESCRIPTION OF THE INVENTION

The electrophotographic photosensitive member of this invention will now be explained in detail.

FIG. 1 to FIG. 4 each is a schematic sectional view showing the layer structure of the electrophotographic photosensitive member of this invention.

Figure 1:
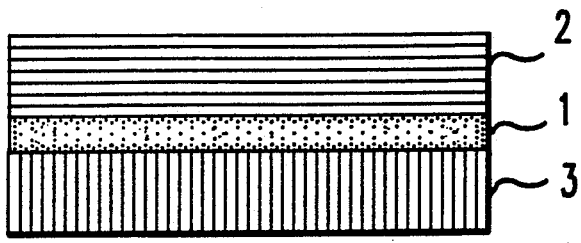
FIG. 1 to FIG. 4 each is a schematic sectional view showing a construction of the electrophotographic photosensitive member of this invention and FIG. 5 to FIG. 7 are graphs showing the infrared absorption spectra of Compounds Ia-2, Ic-11, and Id-11, respectively, produced in Synthetic Examples 1, 2, and 3. In the graphs, the axis of ordinate is a percent transmittance (%) and the axis of abscissa is a wave number ($cm^{-1}$).

In the embodiment of this invention shown in FIG. 1, a charge generating layer 1 and a charge transporting layer 2 are successively formed on a conductive support 3.

Figure 2:
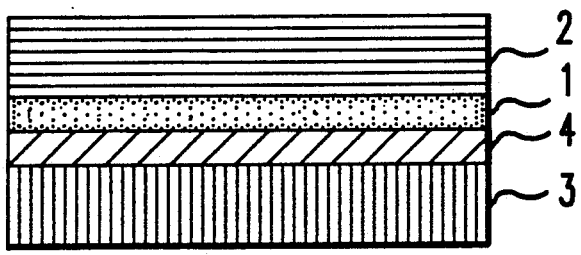

In the embodiment of this invention shown in FIG. 2, an undercoating layer 4 is formed between a conductive support 3 and a charge generating layer 1.

Figure 3:
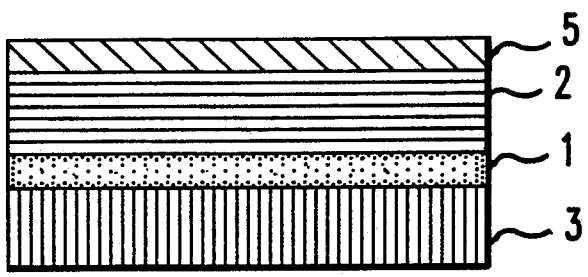

In the embodiment of the invention shown in FIG. 3, a protective layer 5 is formed on the surface of a charge transporting layer 2.

Figure 4:
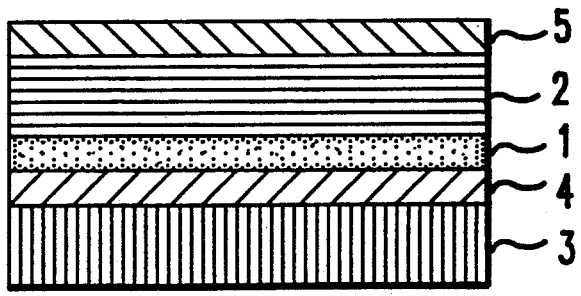

In the embodiment of this invention shown in FIG. 4, an undercoating layer 4 is formed between a conductive support 3 and a charge generating layer 1 and a protective layer 5 is formed on the surface of a charge transporting layer 2.

Now, each layer included in the electrophotographic photosensitive member of this invention will be explained.

As a conductive support 3 for the electrophotographic photosensitive member of this invention, there are a drum of a metal such as aluminum, copper, iron zinc, nickel, etc., and drum-form, sheet-form, or plate-form papers, plastic films or sheets, or glass sheets which are rendered conductive by vapor-depositing thereon a metal film such as any of aluminum, copper, gold, silver, platinum, palladium, titanium, nickel-chromium, stainless steel, copper-indium, etc., or vapor-depositing a conductive metal compound such a dispersion of any of an indium oxide, tin oxide, etc., or laminating thereon a metal foil, or coating thereon a dispersion of any of carbon black, indium oxide, a tin oxide-antimony oxide powder, a metal powder, etc., in a binder resin.

Furthermore, if necessary, various kinds of treatments can be applied onto the surface of a conductive support 3 to overcome adverse influences on the image quality. For example, an oxidation treatment, a chemical treatment or a coloring treatment may be applied onto the surface of a conductive support or a light absorption layer may be formed on the surface thereof or a light-scattering treatment may be applied onto the surface thereof for preventing the formation of interference fringes and other effect of specular reflection occurring in the case of using coherent light such as laser light, etc., for image-forming exposure. As a method for the light-scattering treatment, a sand blast method, a liquid honing method, a grinding stone polishing method, a buff polishing method, a belt-sander method, a brush polishing method, a steel wool polishing method, an acid etching method, an alkali etching method, an electrochemical etching method, etc.

Also, an undercoating layer 4 may be formed between a conductive support 3 and a charge generating layer 1. The undercoating layer shows actions of inhibiting the injection of charges from the conductive support 3 into the photosensitive layer 1 of the double layer type photosensitive member in charging the photosensitive layer and strongly adhering the photosensitive layer 1 to the conductive support 3 as an adhesive layer or shows an action of preventing the reflection of light on the conductive support.

As the binder resin for the undercoating layer 4, there are polyethylene, polypropylene, an acryl resin, a methacryl resin, a polyamide resin, a vinyl chloride resin, a vinyl acetate resin, a phenol resin, a polycarbonate, polyurethane, a polyimide resin, a vinylidene chloride resin, a polyvinyl acetal resin, a vinyl chloride-vinyl acetate copolymer, polyvinyl alcohol, water-soluble polyester, nitrocellulose, casein, gelatin, etc.

The thickness of the undercoating layer 4 is from 0.01 to 10 μm, and preferably from 0.05 to 3 μm.

As a coating method for forming the undercoating layer, there are a blade coating method, a Meyer bar coating method, a spray coating method, a dip coating method, a bead coating method, an air knife coating method, or a curtain coating method.

The charge generating layer 1 constituting a photosensitive layer on the conductive support 3 in this invention contains a charge generating pigment having a positive hole transporting property, at least one of the compounds shown by the above formulae (Ia), (Ib), (Ic), and (Id), and a binder resin.

It is required that the charge generating pigment which is used together with at least one of the compounds shown by the formulae (Ia), (Ib), (Ic), and (Id) has a positive hole transporting property by itself. Whether or not a charge generating pigment has a positive hole transporting property may be determined by a method vapor depositing the pigment on a substrate or coating the pigment on a substrate as a dispersion in a resin at a high concentration, charging the layer positively or negatively, and measuring the light decay of the charge. In this invention, the term "charge generating pigment having a positive hole transporting property" means the pigment showing the large light decay at positively charging as compared to the light decay at negatively charging in the aforesaid determination method.

As the charge generating pigment having a positive hole transporting property, there are squearyrium series pigments, phthalocyanine series pigments, perylene series pigments, etc.

As a first group of specific examples of pigments, from the group of pigments known as the squearyrium series pigments, there are those shown by following formula (II)

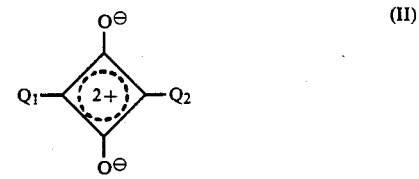

wherein $Q_1$ and $Q_2$ each represents a substituent selected from those shown by the following formulae:

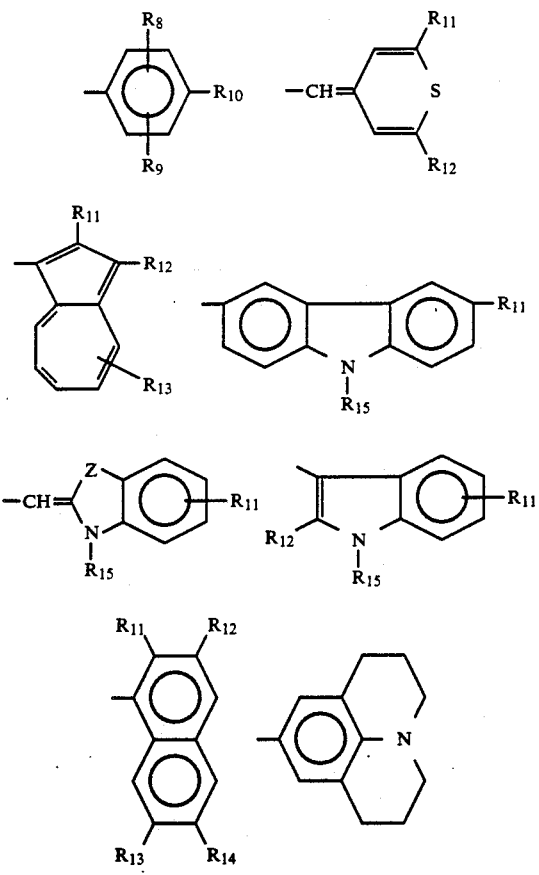

In the above formulae, $R_8$ and $R_9$ each represents a hydrogen atom, a hydroxy group, a fluorine atom, an alkyl group, —$NR_{16}R_{17}$ (wherein $R_{16}$ and $R_{17}$ each represents a hydrogen atom, an alkyl group, an aryl group, an aralkyl group, an alkylcarbonyl group, or an arylcarbonyl group), an alkoxy group, or an aryloxy group; $R_{10}$ represents —$NR_{18}R_{19}$ (wherein $R_{18}$ and $R_{19}$ each represents an alkyl group, an aryl group, or an aralkyl group); $R_{11}$ to $R_{14}$ each represents a hydrogen atom, an alkyl group, an aryl group, —$CONHR_{20}$ (wherein $R_{20}$ represents an alkyl group, an aryl group, or an aralkyl group), a halogen atom, an alkoxy group, or an aryloxy group; $R_{15}$ represents an alkyl group, an aryl group, or an aralkyl group; and Z represents

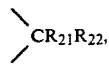

—S—, or —$CR_{21}$=$CR_{22}$— (wherein $R_{21}$ and $R_{22}$ each represents a hydrogen atom, an alkyl group, an aryl group, or an aralkyl group).

Specific examples of the squearyrium series pigments are illustrated below.

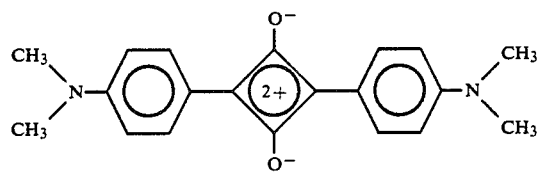

II-1

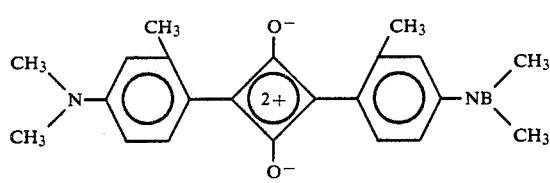

II-2

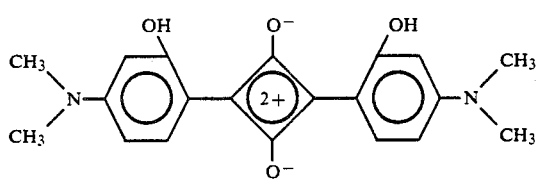

II-3

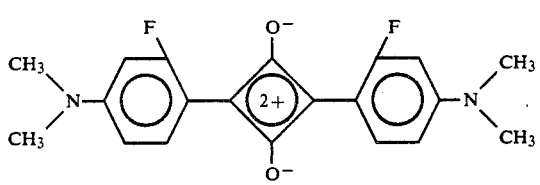

II-4

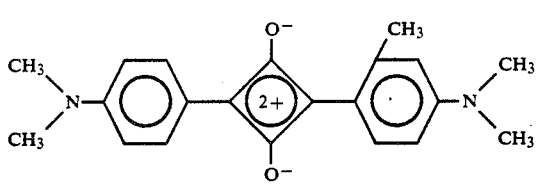

II-5

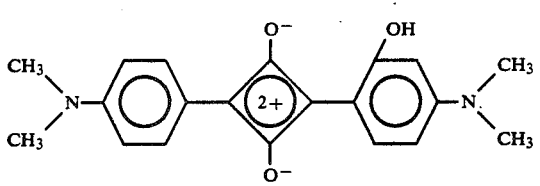

II-6

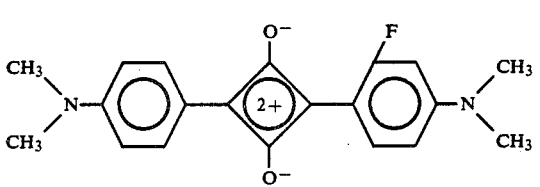

II-7

-continued
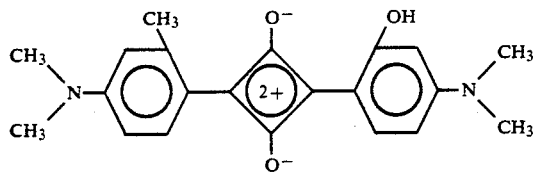 II-8
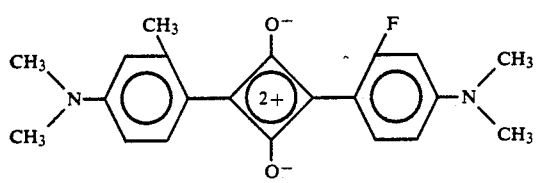 II-9
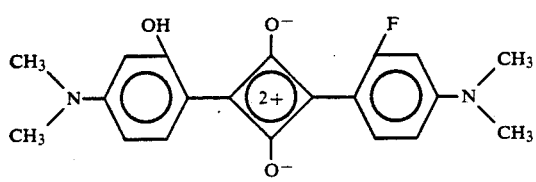 II-10
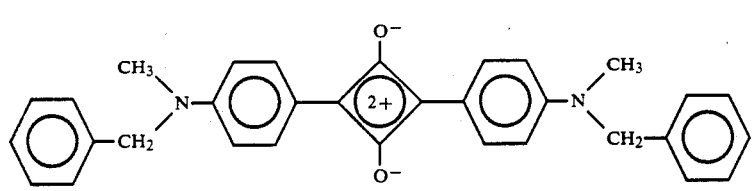 II-11
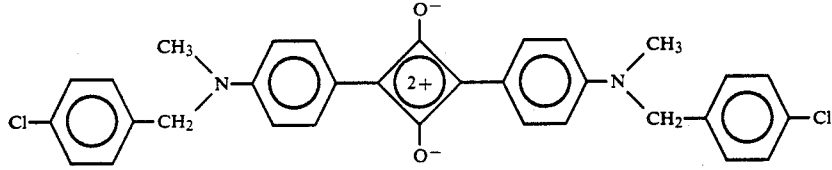 II-12
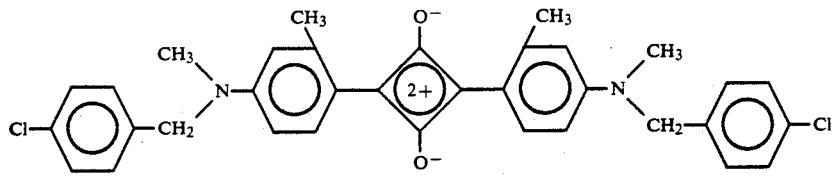 II-13
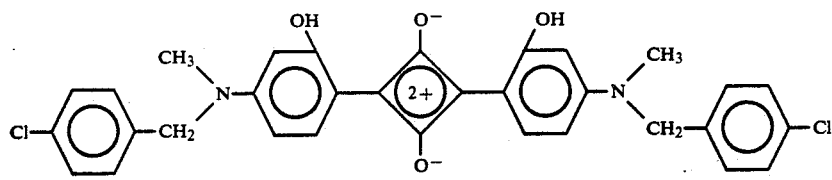 II-14
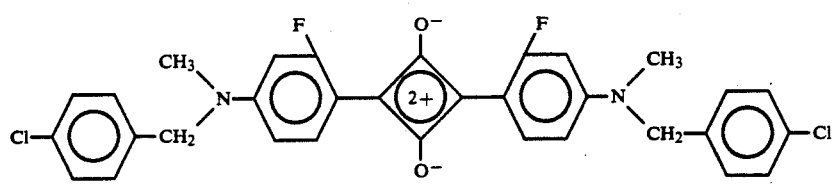 II-15
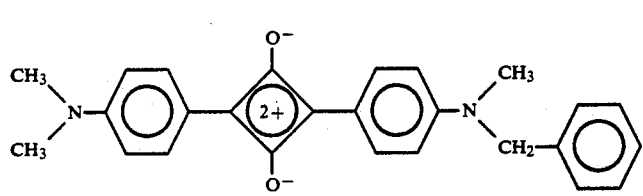 II-16

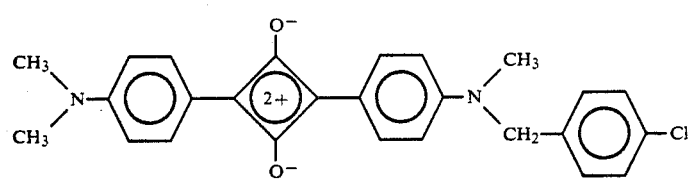 II-17
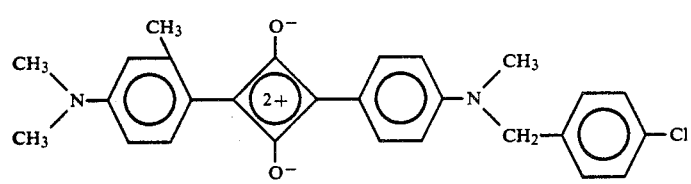 II-18
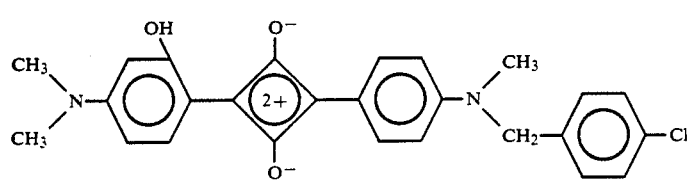 II-19
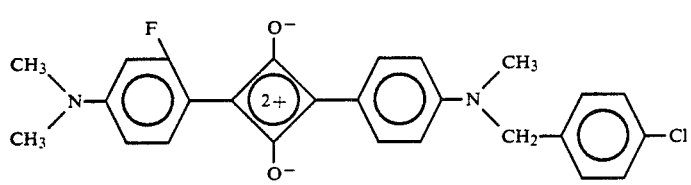 II-20
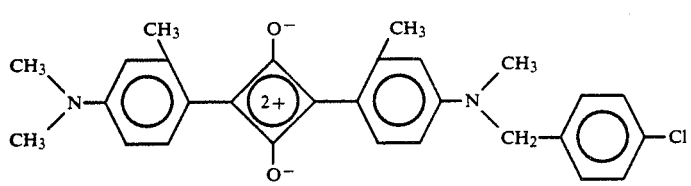 II-21
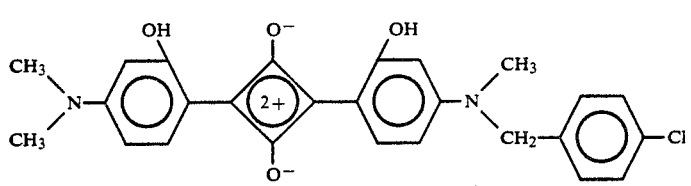 II-22
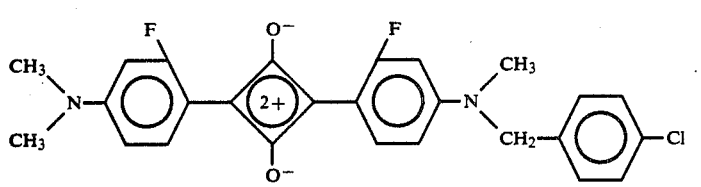 II-23
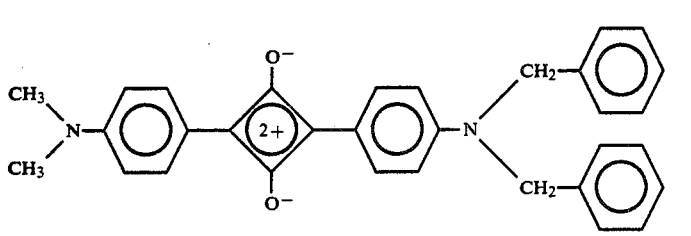 II-24

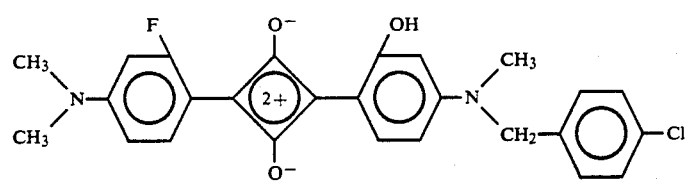
II-25
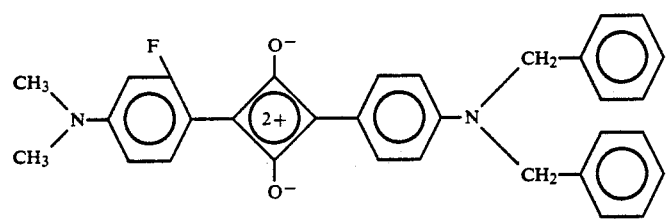
II-26
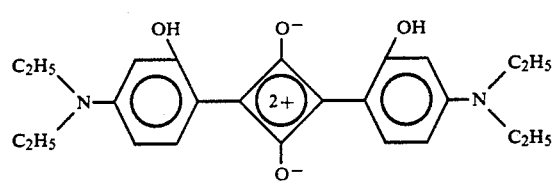
II-27
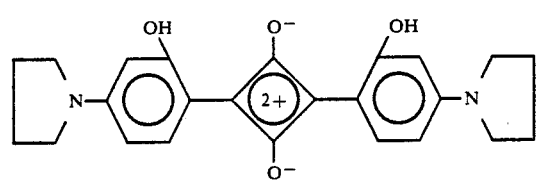
II-28
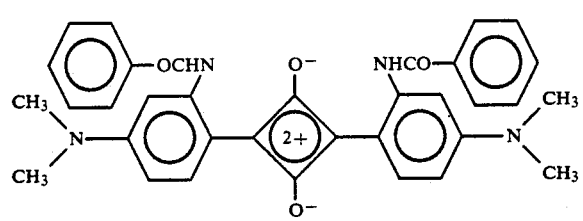
II-29
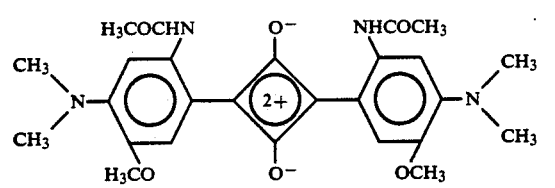
II-30
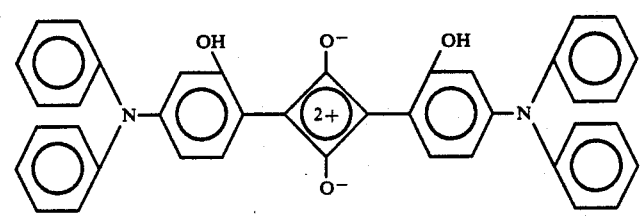
II-31

II-32
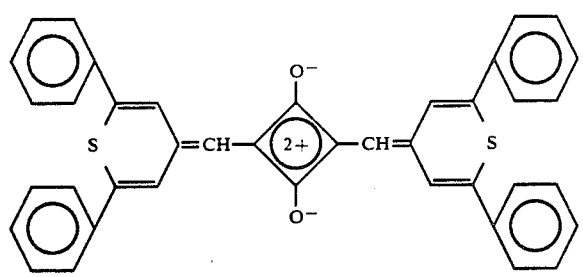
II-33
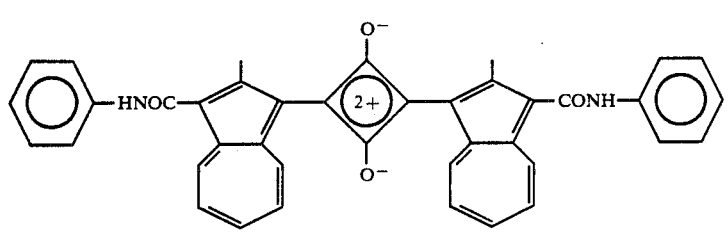
II-34
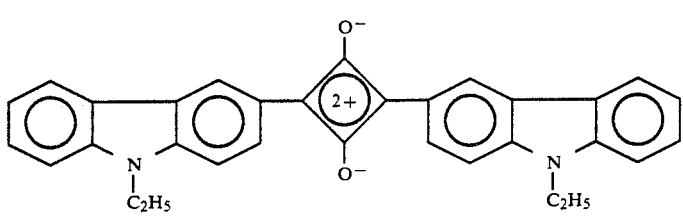
II-35
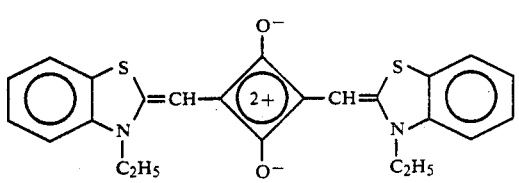
II-36
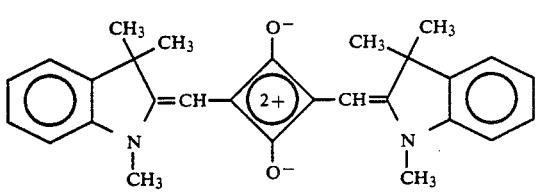
II-37
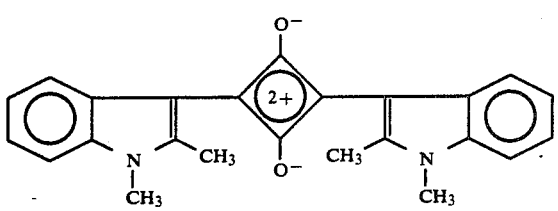
II-38
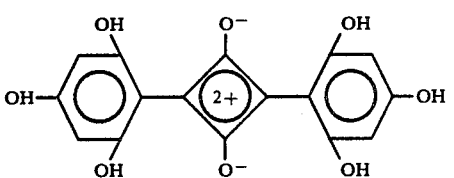

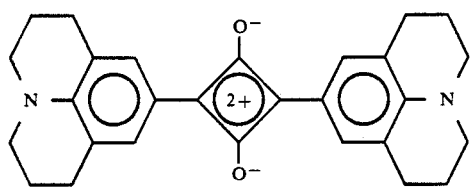

II-39

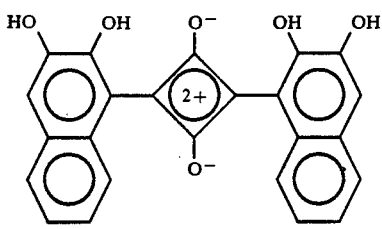

II-40

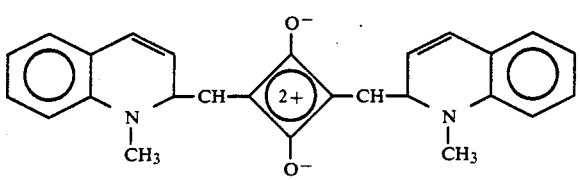

II-41

As a second group of specific examples of pigments, from the group of pigments known as the phthalocyanine series pigments, there are those shown by following formula (III)

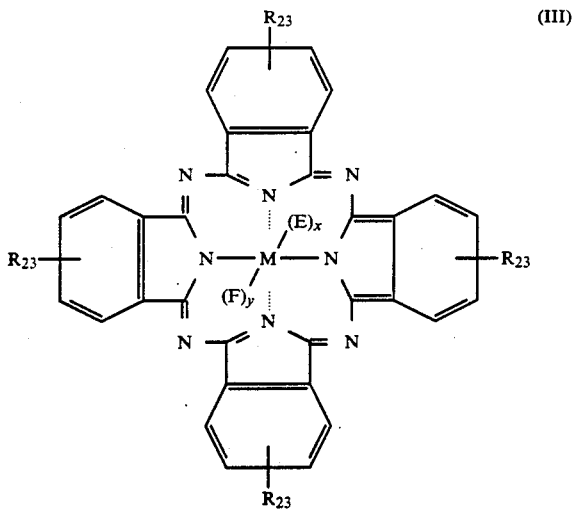

(III)

wherein $R_{23}$ represents a hydrogen atom, an alkyl group, an aryl group, an aralkyl group, a halogen atom, a cyano group, or a nitro group; M represents two hydrogen atoms or a metal atom selected from Cu, Ni, Co, Fe, Mn, Cr, Ti, Ru, Pd, In, Sn, Sb, Zn, Mg, Ga, Ge, As, Si, Hg, Ti, V, U, and Pd; E and F each represents a halogen atom or an oxygen atom; and x and y each represents 0 or 1; provided that, when M is a divalent metal atom, x and y each shows 0; when M is a trivalent metal atom, x shows 1 and y shows 0; when M is a tetravelent metal atom, x and y each represents 1; when M is V, E shows an oxygen atom, x shows 1, and y shows 0; and when M is V, E and F each represents an oxygen atom and x and y each represents 1.

Specific examples of the pigment are non-metal phthalocyanine, copper phthalocyanine, vanadyl phthalocyanine, titanyl phthalocyanine, aluminum phthalocyanine, gallium phthalocyanine, indium phthalocyanine, thallium phthalocyanine, silicon phthalocyanine, germanium phthalocyanine, tin phthalocyanine, lead phthalocyanine, and the halides of the aforesaid phthalocyanines.

As a third group of specific examples of pigments, from the group of pigments known as the perylene series pigments, there are those shown by following formula (IV)

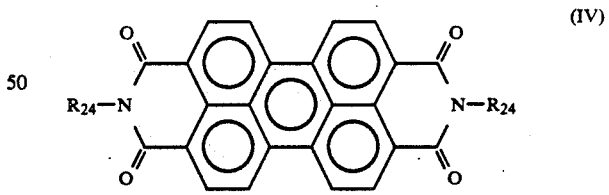

(IV)

wherein $R_{24}$ represents an alkyl group, an aryl group, or an aralkyl group, these groups may be substituted.

Specific examples of the perylene pigment are illustrated below.

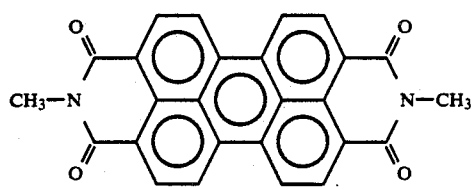

IV-1

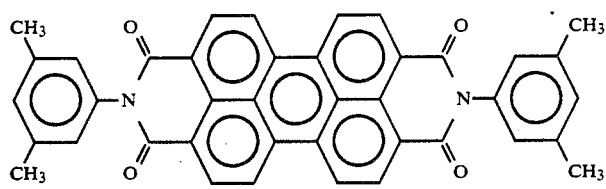
IV-2
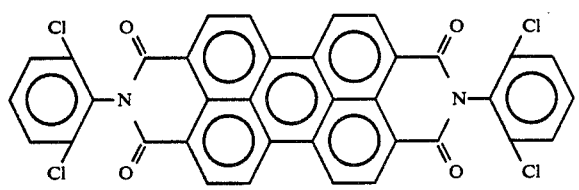
IV-3
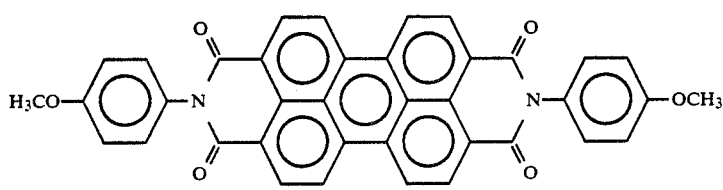
IV-4
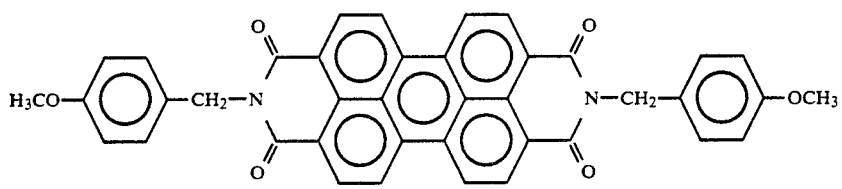
IV-5
On the other hand, specific examples of the tetracyanoanthraquinodimethane compound, which is deposited with the charge-generating pigment in the charge-generating layer 1, and which is shown by formula (Ia) described above, are illustrated below.
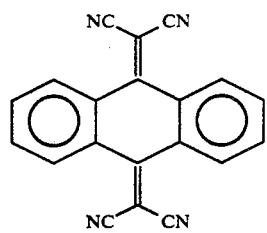
Ia-1
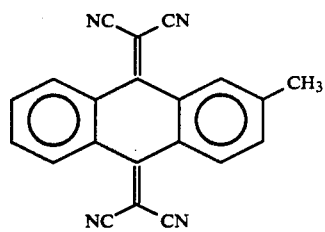
Ia-2
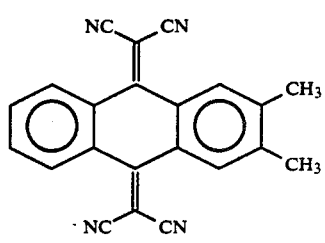
Ia-3
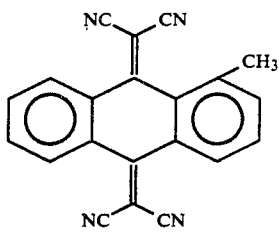
Ia-4
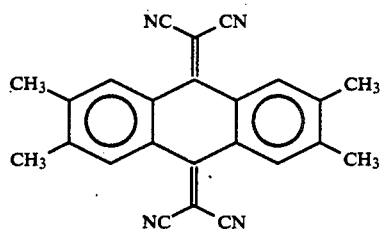
Ia-5
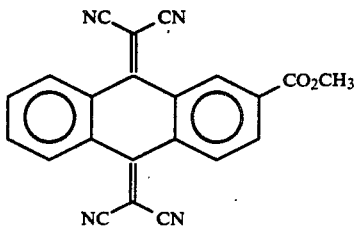
Ia-6

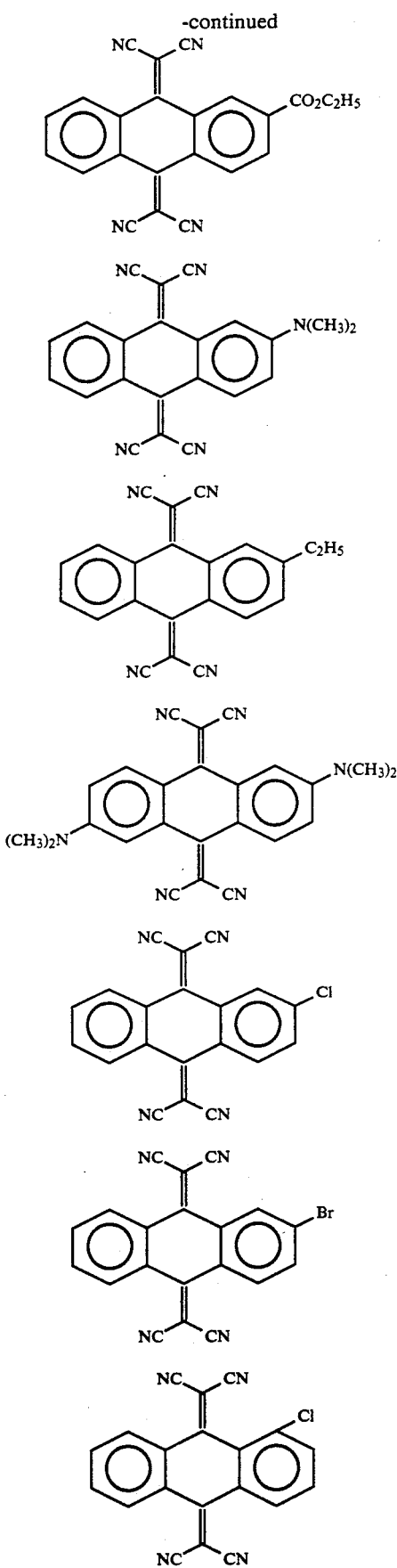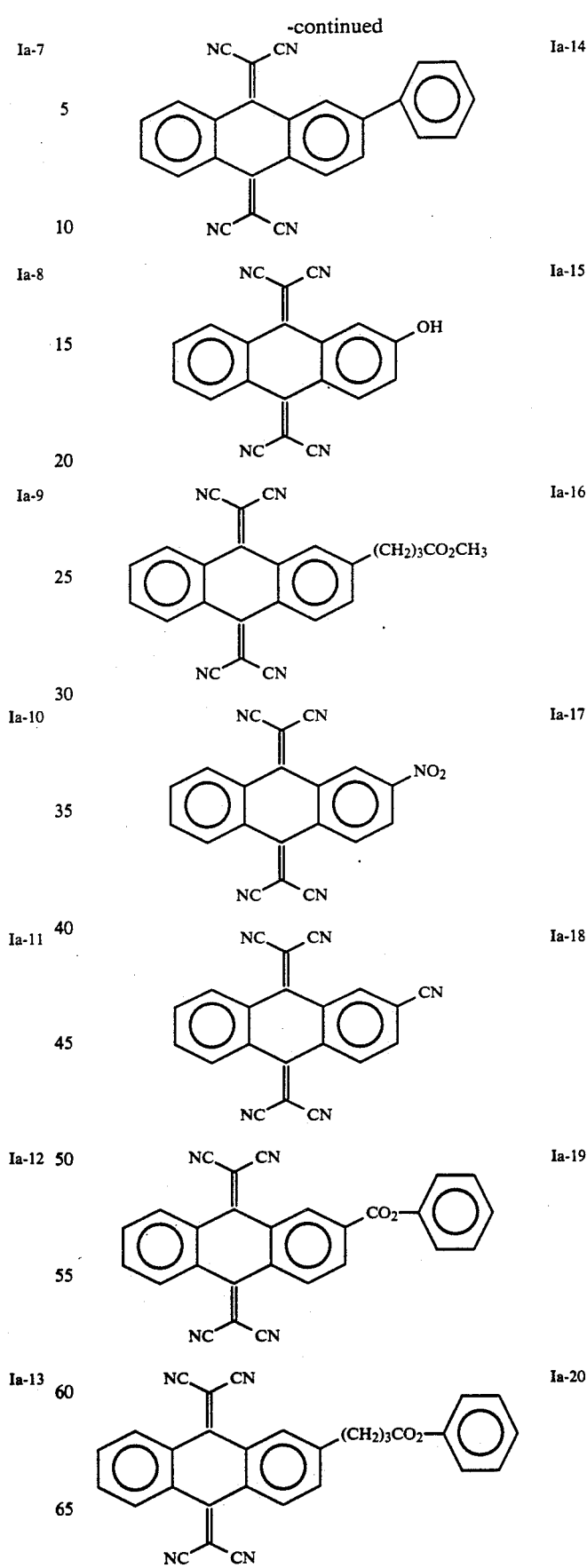

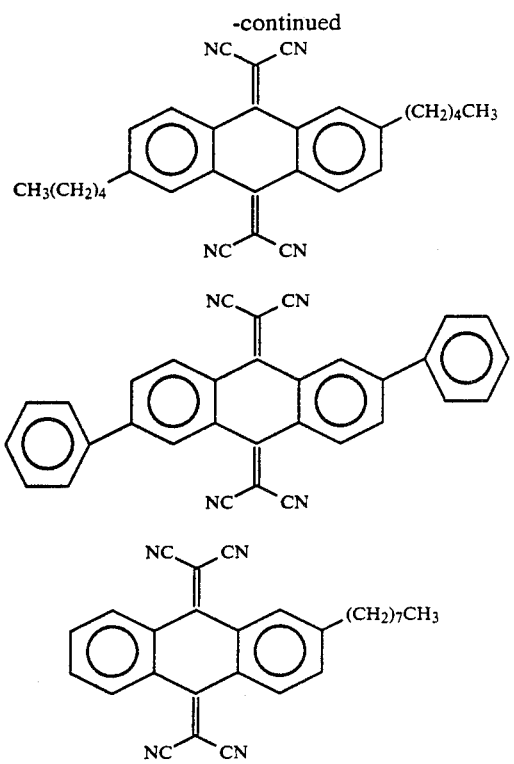
Ia-21
Ia-22
Ia-23
Specific examples of the anthraquinone compound, which is deposited with charge-generating pigment in charge-generating layer 1, and which is shown by formula (Ib) described above, are illustrated below.
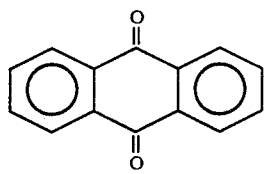
Ib-1
Ib-2
Ib-3
Ib-4
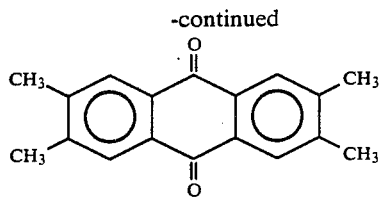
Ib-5
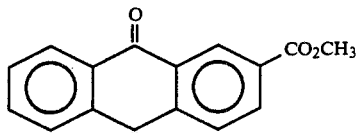
Ib-6
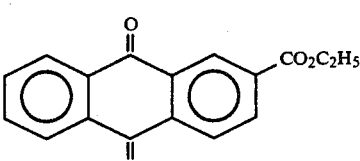
Ib-7
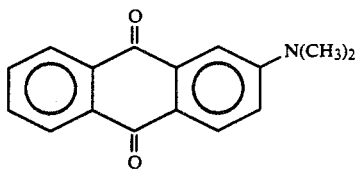
Ib-8
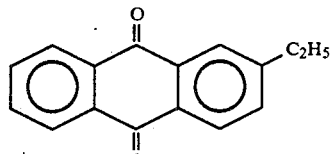
Ib-9
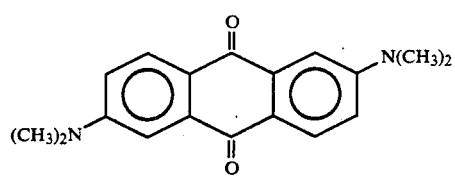
Ib-10
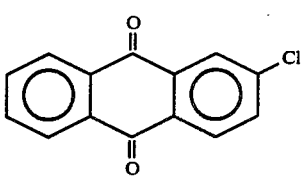
Ib-11
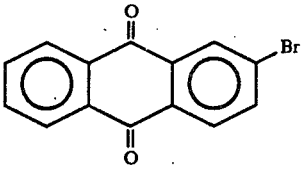
Ib-12
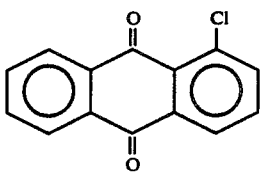
Ib-13

-continued
Ib-14 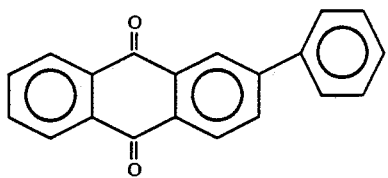
Ib-15 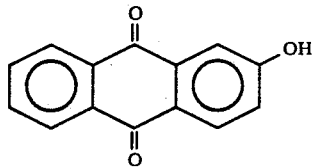
Ib-16 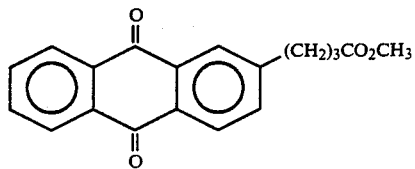
Ib-17 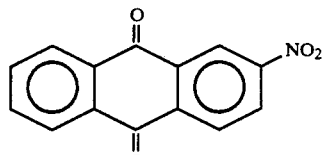
Ib-18 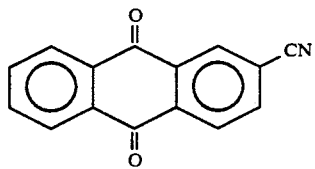
Ib-19 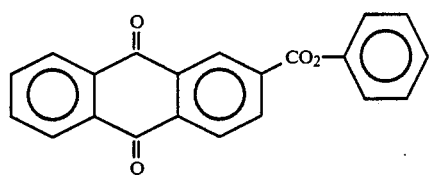
Ib-20 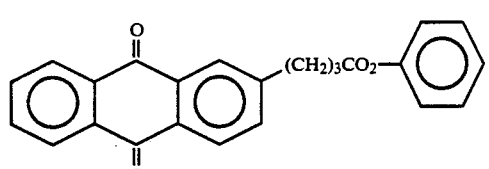
Ib-21 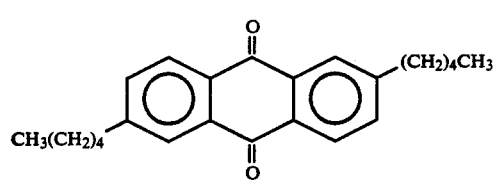
Ib-22 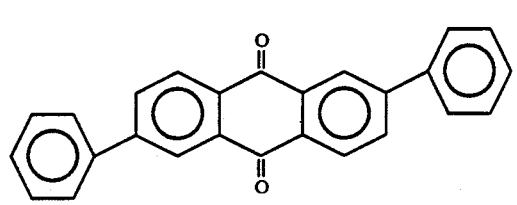
-continued
Ib-23 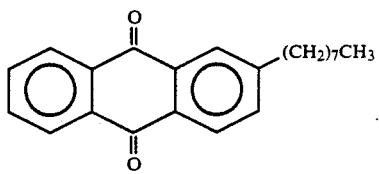
Specific examples of the dicyanovinyl compound, which is deposited with the charge-generating pigment in the charge-generating layer 1, and which is shown by formula (Ic) described above, are illustrated below.
Ic-1 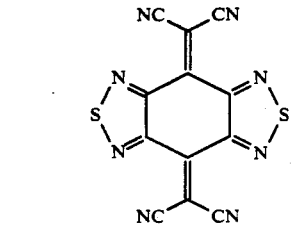
Ic-2 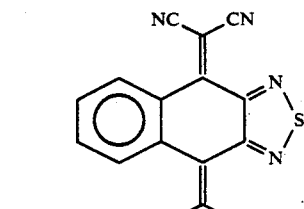
Ic-3 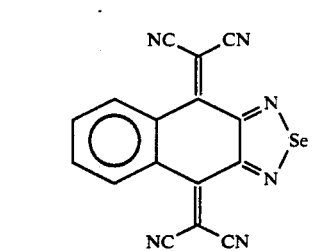
Ic-4 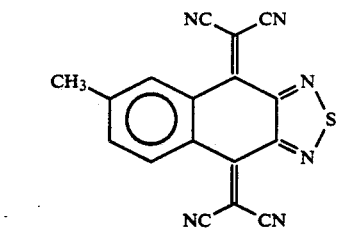
Ic-5 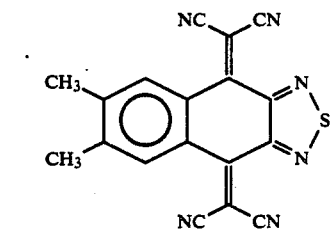

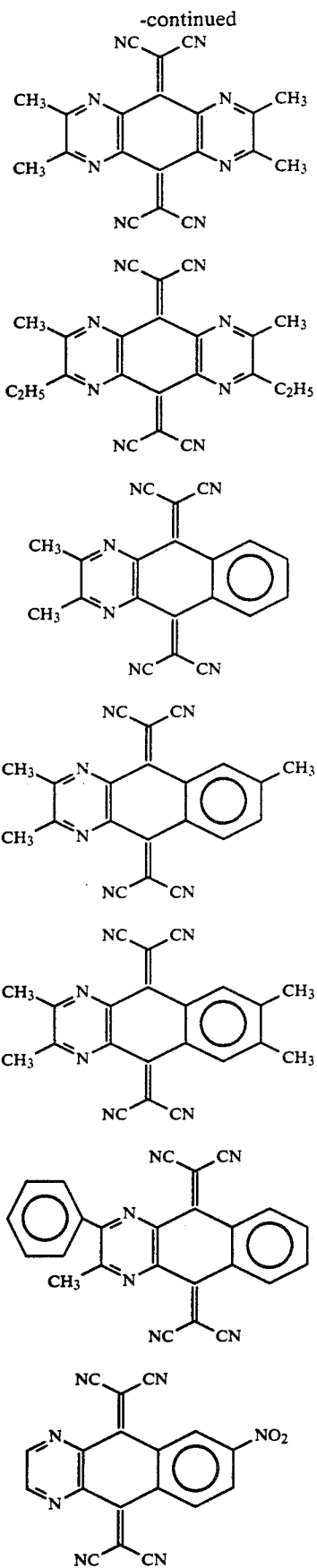
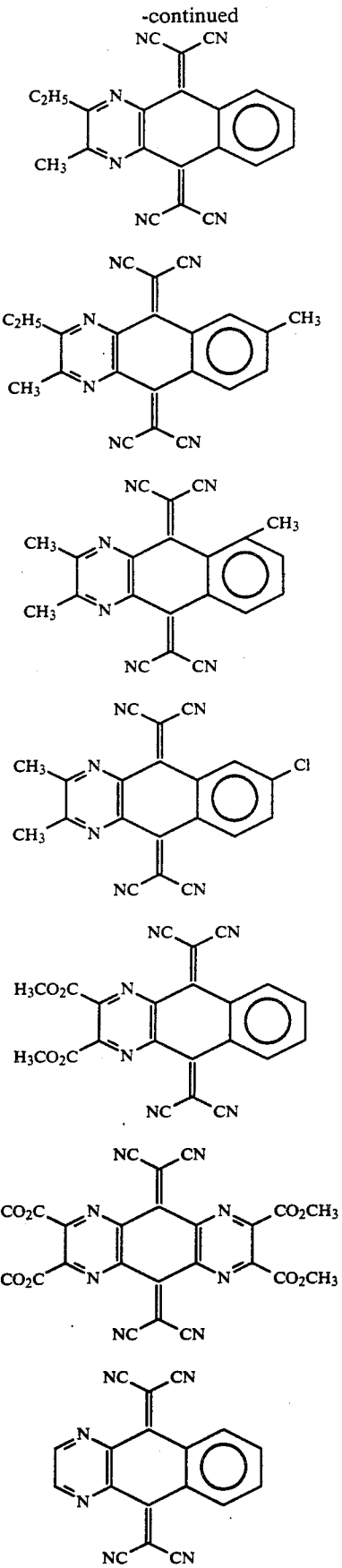

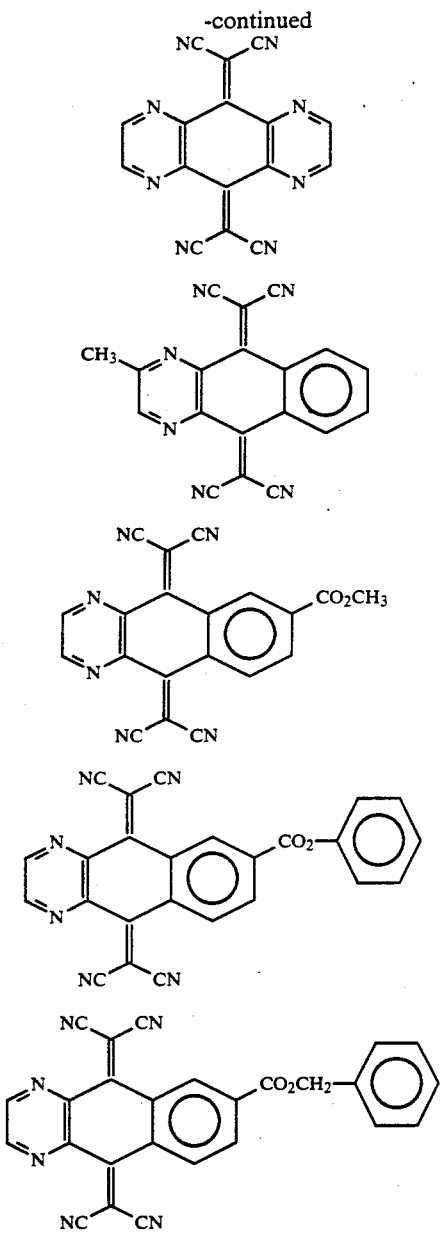
Also, specific examples of the quinone compound, which is deposited with the charge-generating pigment in the charge-generating layer 1, and which is shown by formula (Id), are illustrated below.
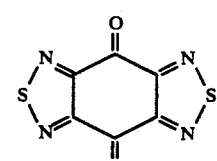
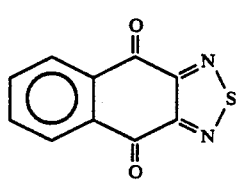
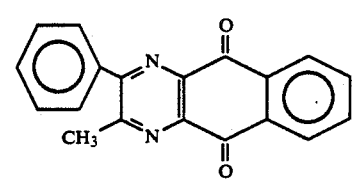

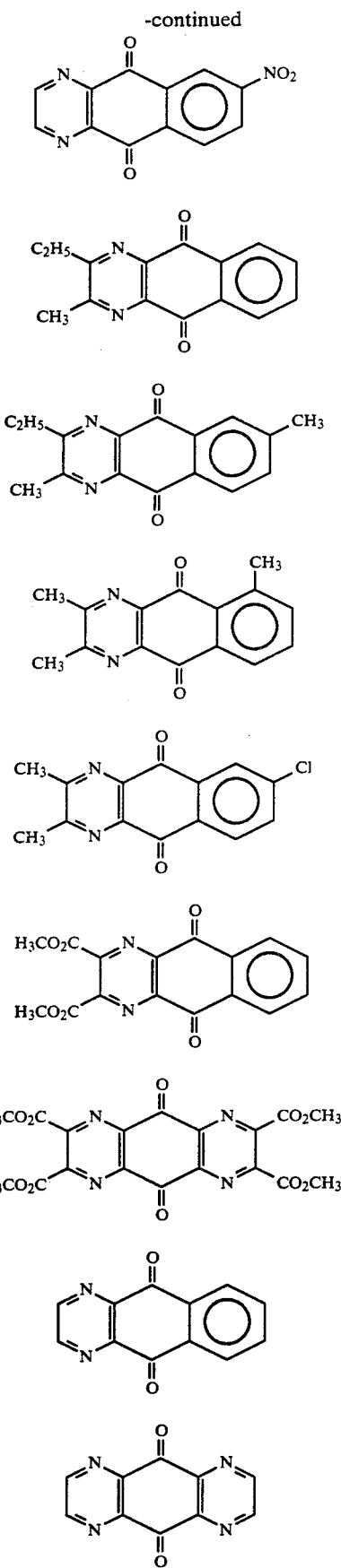
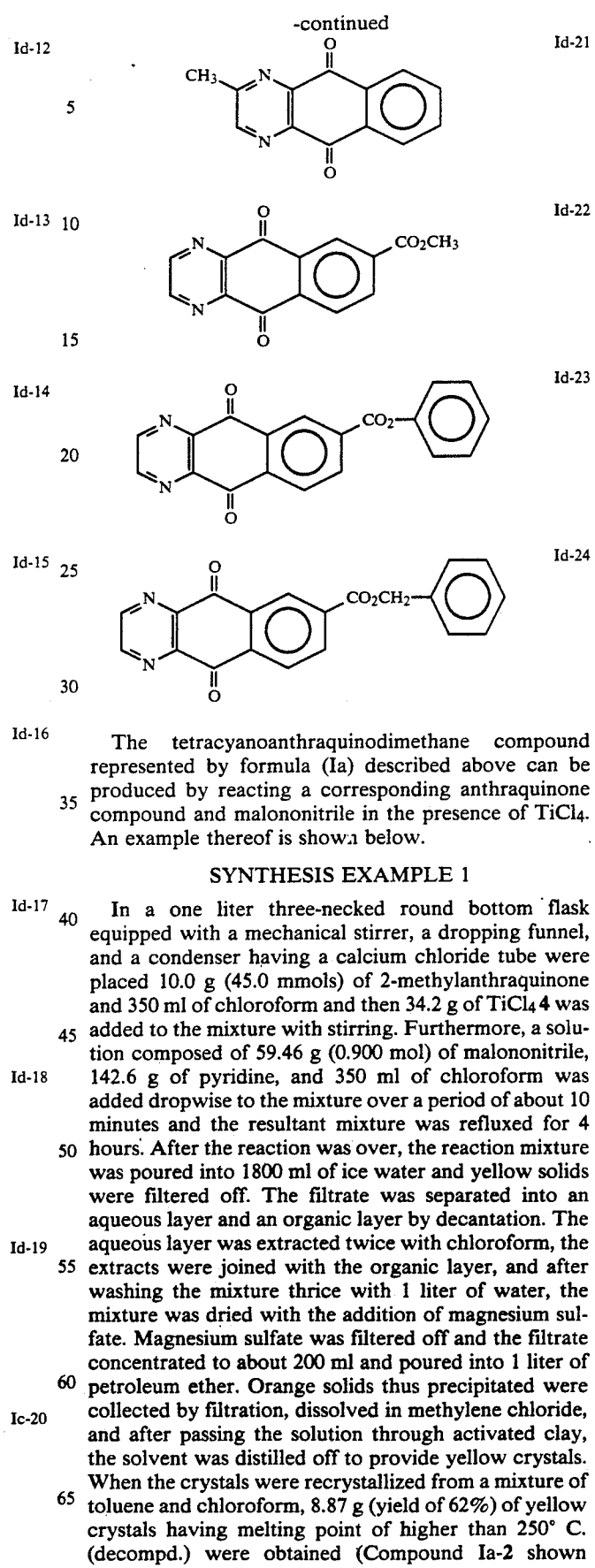

The tetracyanoanthraquinodimethane compound represented by formula (Ia) described above can be produced by reacting a corresponding anthraquinone compound and malononitrile in the presence of TiCl₄. An example thereof is shown below.

SYNTHESIS EXAMPLE 1

Figure 5:
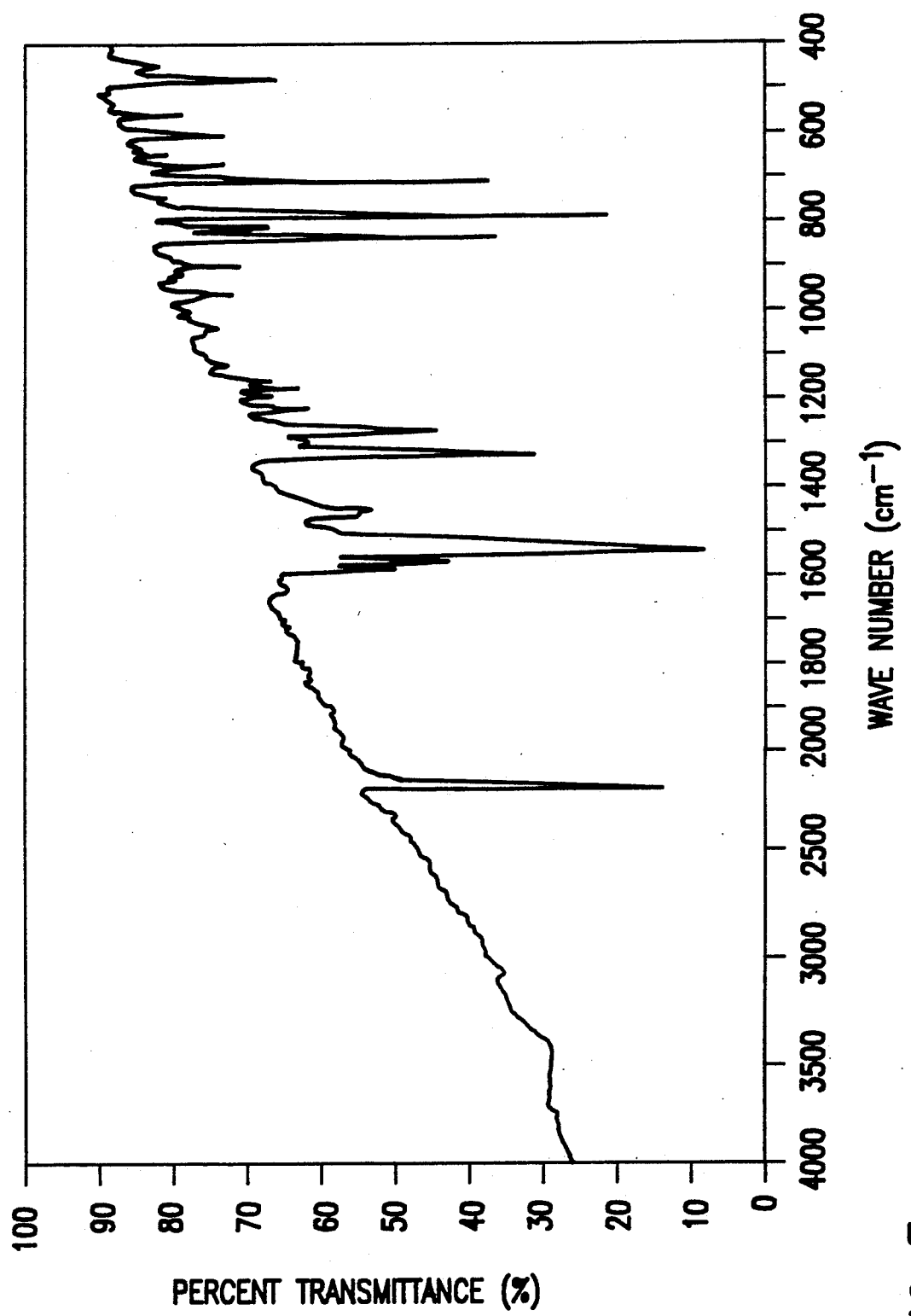

In a one liter three-necked round bottom flask equipped with a mechanical stirrer, a dropping funnel, and a condenser having a calcium chloride tube were placed 10.0 g (45.0 mmols) of 2-methylanthraquinone and 350 ml of chloroform and then 34.2 g of TiCl₄ 4 was added to the mixture with stirring. Furthermore, a solution composed of 59.46 g (0.900 mol) of malononitrile, 142.6 g of pyridine, and 350 ml of chloroform was added dropwise to the mixture over a period of about 10 minutes and the resultant mixture was refluxed for 4 hours. After the reaction was over, the reaction mixture was poured into 1800 ml of ice water and yellow solids were filtered off. The filtrate was separated into an aqueous layer and an organic layer by decantation. The aqueous layer was extracted twice with chloroform, the extracts were joined with the organic layer, and after washing the mixture thrice with 1 liter of water, the mixture was dried with the addition of magnesium sulfate. Magnesium sulfate was filtered off and the filtrate concentrated to about 200 ml and poured into 1 liter of petroleum ether. Orange solids thus precipitated were collected by filtration, dissolved in methylene chloride, and after passing the solution through activated clay, the solvent was distilled off to provide yellow crystals. When the crystals were recrystallized from a mixture of toluene and chloroform, 8.87 g (yield of 62%) of yellow crystals having melting point of higher than 250° C. (decompd.) were obtained (Compound Ia-2 shown above). The infrared spectrum of the compound is shown in FIG. 5.

The dicyanovinyl compound shown by formula (Ic) shown above can be synthesized by reacting a corresponding quinone compound and malononitrile in a solvent. An example thereof is shown below.

SYNTHESIS EXAMPLE 2

In a 200 ml Erlenmeyer flask were placed 5.0 g (26.5 mmols) of 2,3-diaminonaphthoquinone and 75 ml of acetic acid/water (1/1), then a solution composed of 5.9 g (39.8 mmols) of 1-phenyl-1,2-propanedione and 25 ml of acetic acid/water (1/1) was added dropwise to the mixture under ice-cooling over a period of about 10 minutes, and after stirring the mixture for 5 minutes, yellow precipitates formed were collected by filtration and washed with water. The precipitates were dissolved in methylene chloride; and, after purifying the solution by silica gel short column (eluted by methylene chloride), the product obtained was recrystallized from methylene chloride-methanol to provide 6.22 g (yield 78%) of 2-methyl-3-phenylnaphthoquinone as a yellow powder. Melting point 235°-236° C.

Figure 6:
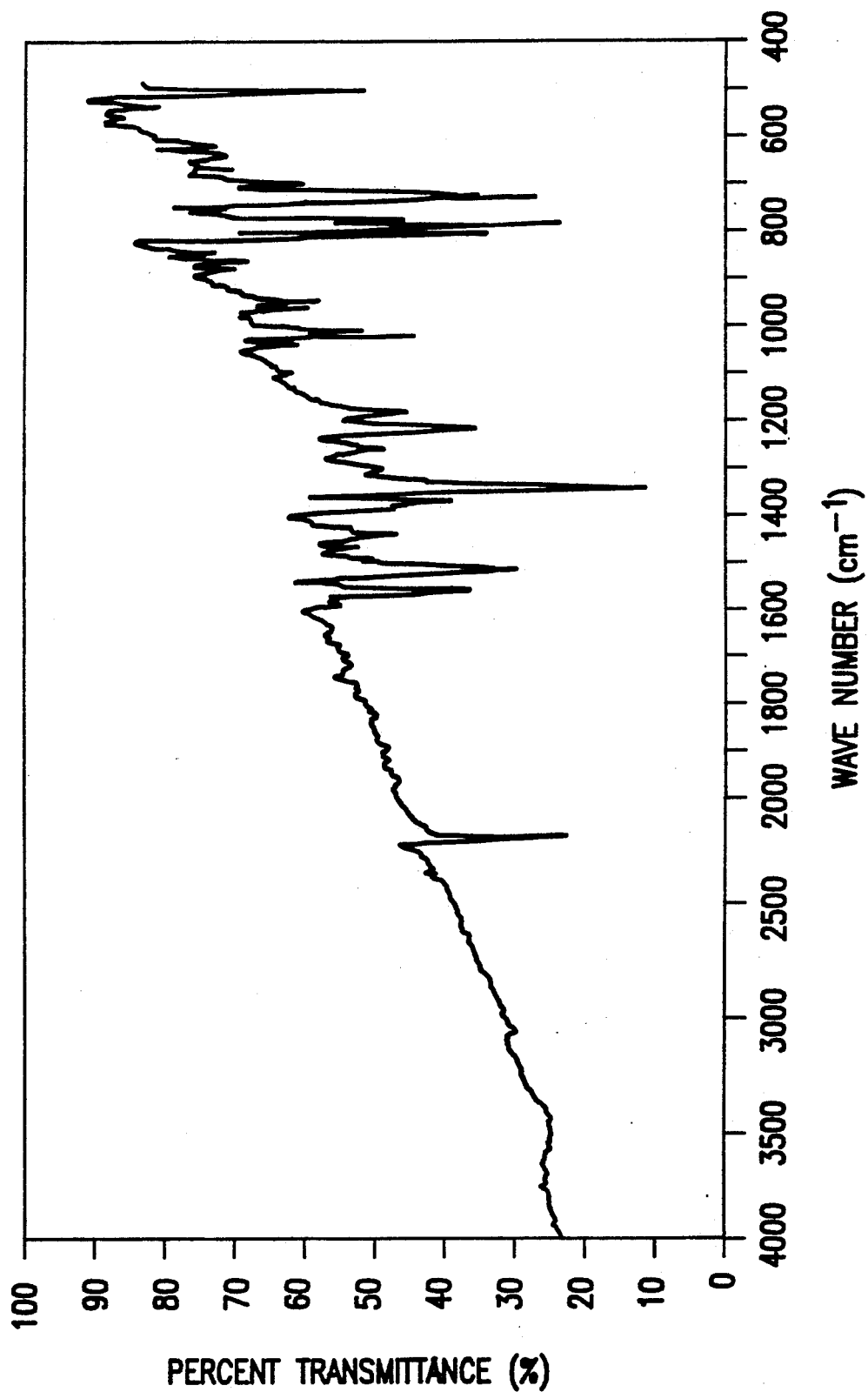

In a 500 ml three-necked flask were placed 3.36 g (11.2 mmols) of the compound obtained above and 160 ml of chloroform and after cooling the mixture to −20° C. under nitrogen gas stream, 5.1 ml of $TiCl_4$ was added to the mixture. Then, a solution composed of 2.15 g (32.5 mmols) of malononitrile, 17 ml of pyridine, and 80 ml of chloroform was added dropwise to the mixture over a period of about 30 minutes and after further stirring the mixture for 2 hours, the temperature was allowed to rise to room temperature followed by stirring for further 13 hours. Then, 200 ml of water was added to the reaction mixture, after filtering the mixture through zeolite, an organic phase was separated therefrom, and after drying the organic phase with sodium sulfate, the solvent was distilled off under reduced pressure to provide brown solids. The solids were purified by silica gel short column (eluted by methylene chloride) and recrystallized from a mixture of methylene chloride and n-hexane to provide 3.31 g (yield 74.5%) of Compound (Ic-11) as a yellow powder having melting point of 225° C. (decomp.). The infrared spectrum of the compound obtained is shown in FIG. 6.

The quinone compounds shown by formula (Id) described above can be synthesized by known methods. An example thereof is shown below.

SYNTHESIS EXAMPLE 3

Figure 7:
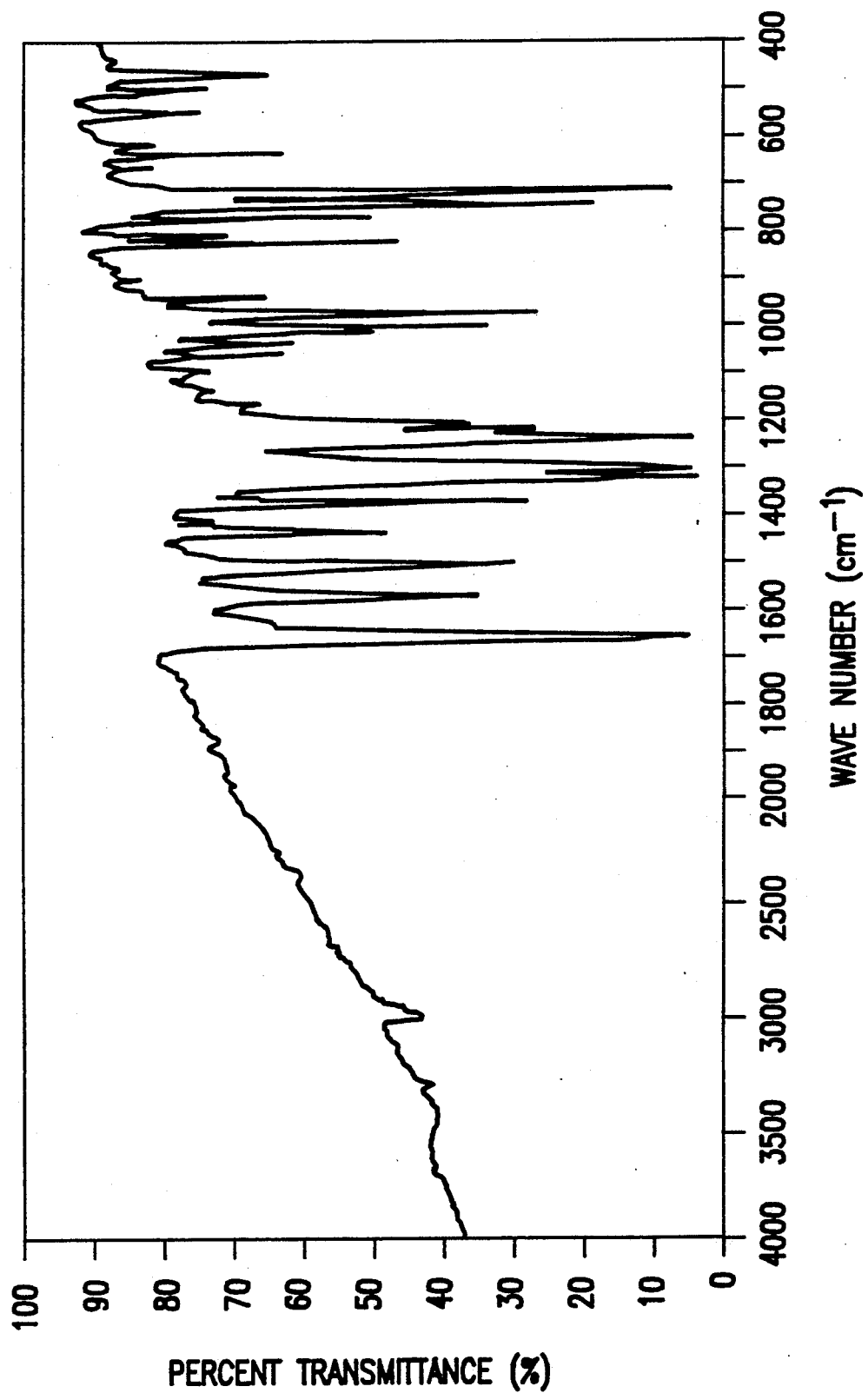

In a 200 ml of Erlenmeyer flask were placed 5.0 g (26.5 mmols) of 2,3-diaminonaphthoquinone and 75 ml of acetic acid/water (1/1), a solution composed of 5.9 g (39.8 mmols) of 1-phenyl-1,2-propanedione and 25 ml of acetic acid/water (1/1) was added dropwise to the mixture under ice-cooling over a period of about 10 minutes, and after stirring the mixture for 5 minutes, yellow precipitates thus formed were collected by filtration and washed with water. The precipitates were dissolved in methylene chloride, and after purifying the product with silica gel short column (eluted by methylene chloride), the product was recrystallized from methylene chloridemethanol to provide 6.22 g (78%) of 2-methyl-3-phenylnaphthoquinone (Compound Id-11) as a yellow powder. Melting point 235°-236° C. The infrared spectrum of the compound obtained is shown in FIG. 7.

As the binder resin for the aforesaid charge generating pigment having the positive hole transporting property and at least one of the aforesaid compounds shown by formulae (Ia), (Ib), (Ic), and (Id) described above hereinafter, the compound is referred to as a compound of formula (I)], there are polystyrene, silicone resins, polycarbonate resins, acryl resins, methacryl resins, polyester, vinyl series resins, celluloses, alkyd resins, etc.

In the charge generating layer 1 in this invention, the compound of formula (I) is incorporated therein in the range of from 0.01 to 2 molar equivalents, and preferably from 0.1 to 1 molar equivalent, to the amount of the charge generating pigment having the positive hole transporting property. If the proportion of the compound of formula (I) is less than 0.01 equivalent, the aforesaid effects for the increase of photosensitivity and the reduction of the potentials at the exposed portions and unexposed portions by the change of surrounding conditions and by repeated use become less, while if the proportion thereof is over 2 equivalents, the dark decay is greatly increased, the charged potential is lowered, and the background portions are liable to be fogged in an electrophotographic process of forming toner images at the unexposed portion. Thus, the aforesaid range is preferred.

Also, it is preferred that the charge generating pigment having a positive hole transporting property is incorporated in the layer in the range of from 0.1 to 10 parts by weight to 1 part by weight of the binder resin.

For incorporating the charge generating pigment having the positive hole transporting property and the compound of formula (I) described above in the charge generating layer 1, various methods can be employed. For example, there are following methods.

(1) The charge generating pigment having the positive hole transporting property and the compound of formula (I) are dispersed together in a solvent solution of the binder resin. As the dispersion method, an ordinary method such as a ball mill dispersion method, an attriter dispersion method, a sand mill dispersion method, a ultrasonic dispersion method, etc., can be used.

(2) The charge generating pigment having the positive hole transporting property is first dispersed in a solvent solution of the binder resin and then the compound of formula (I) is added to the dispersion thus formed.

(3) The charge generating pigment having the positive hole transporting property is treated with a solution of the compound of formula (I) to adsorb the compound on the pigment and then the pigment having the compound of formula (I) adsorbed thereon is dispersed in a solvent solution of the binder resin.

(4) The charge generating pigment having the positive hole transporting property is dispersed in a solvent solution of the binder resin, a film of the dispersion is formed by coating, and then the film is treated with a solution of the compound of formula (I), whereby the film is impregnated with the solution of the compound.

In the case of dispersing the charge generating pigment, it is effective that mean particle size (diameter) of the particles of the charge generating pigment is not larger than 3 μm, and preferably not larger than 0.5 μm.

As the solvent which is used at dispersing the aforesaid component(s), ordinary organic solvents such as methanol, ethanol, n-propanol, n-butanol, benzyl alcohol, methylcellosolve, ethylcellosolve, acetone, methyl ethyl ketone, cyclohexane, methyl acetate, dioxane, tetrahydrofuran, methylene chloride, chloroform, etc., can be used singly or as a mixture thereof.

As a coating method for forming the charge generating layer 1, an ordinary method such as a blade coating method, a Meyer bar coating method, a spray coating method, a dip coating method, a bead coating method, an air knife coating method, a curtain coating method, etc., can be used.

The thickness of the charge generating layer is in the range of generally from 0.05 to 5 μm, and preferably from 0.1 to 2.0 μm.

The charge transporting layer 2 in the electrophotographic photosensitive member of this invention is formed by incorporating a charge transporting material in a proper binder resin.

As the charge transporting material, there are oxadiazole derivatives such as 2,5-bis(p-diethylaminophenyl)-1,3,4-oxadiazole, etc., pyrazoline derivatives such as 1,3,5-triphenylpyrazoline, 1-[pyridyl-(2)]-3-(p-diethylaminostyryl)-5-(p-diethylaminophenyl)pyrazoline, etc., aromatic tertiary amino compounds such as triphenylamine, dibenzylaniline, etc., aromatic tertiary diamino compounds such as N,N'-bis(3-methylphenyl)-[1,1'-biphenyl]-4,4'-diamine, etc., 1,2,4-triazine derivatives such as 3-(4'-dimethylaminophenyl)-5,6-di-(4'-methoxyphenyl)-1,2,4-triaazine, etc., hydrazone derivatives such as 4-diethylaminobenzaldehyde-1,1'-diphenylhydrazone, etc., quinazoline derivatives such as 2-phenyl-4-styrylquinazoline, etc., benzofuran derivatives such as 6-hydroxy-2,3-di-(p-methoxyphenyl)benzofuran, etc., α-stilbene derivatives such as p-(2,2-diphenylvinyl)-N,N-diphenylaniline, etc., enamine derivatives described in *Journal of Imaging Science*, Vol. 29, 7-10(1985), carbazole derivatives such as N-ethylcarbazole, etc., poly-N-vinylcarbazole and derivatives thereof, poly-γ-carbazolylethyl glutamate and derivatives thereof and further pyrene, polyvinylpyrene, polyvinylanthracene, polyvinylacrydine, poly-9-biphenylanthracene, a pyreneformaldehyde resin, an ethylcarbazole-formaldehyde resin, etc., although the invention is not limited to them. They can be used singly or as a mixture thereof.

As the binder resin for the charge transporting layer 2, there are polycarbonate resins, polyester resins, polyarylate resins, methacryl resins, acryl resins, vinyl chloride resins, polyvinylacetal resins, a styrenebutadiene copolymer, a vinylidene chloride-acrylonitrile copolymer, a vinyl chloride-vinyl acetate copolymer, a vinyl chloride-vinyl acetate-maleic anhydride terpolymer, silicon resins, silicon-alkyd resins, phenol-formaldehyde resins, styrene-alkyd resins, poly-N-vinylcarbazole, etc., although the invention is not limited to them. These resin binders can be used singly or as a mixture thereof.

The compounding ratio of the charge generating material to the binder resin is preferably from 10:1 to 1:5 (by weight). The thickness of the charge transporting layer 2 is generally from 5 to 50 μm, and preferably from 10 to 30 μm.

As a coating method for forming the charge transporting layer 2, an ordinary method such as a blade coating method, a Meyer bar coating method, a spray coating method, a dip coating method, a bead coating method, a curtain coating method, etc., can be employed.

Furthermore, as a solvent which is used for forming the charge transporting layer 2, aromatic hydrocarbons such as benzene, toluene, xylene, chlorobenzene, etc., ketones such as acetone, 2-butanone, etc., halogenated hydrocarbons such as methylene chloride, chloroform, ethylene chloride, etc., and cyclic or straight chain ethers such as tetrahydrofuran, ethyl ether, etc., can be used singly or as a mixture thereof.

In the electrophotographic photosensitive member of this invention, if necessary, a protective layer 5 may be formed on the charge transporting layer 2. The protective layer 5 is used for preventing the charge transporting layer 2 from being chemically denatured in charging the photosensitive layer 2 of the multilayer type electrophotographic photosensitive member and improving the mechanical strength of the photosensitive layer.

The protective layer 5 is formed by incorporating a conductive material in a proper binder resin. As the conductive material, there are metallocene compounds such as N,N'-dimethylferrocene, etc., aromatic amino compounds such as N'N'-diphenyl-N,N'-bis(3-methylphenyl)-[1,1'-phenyl]-4,4'-diamine, etc., and metal oxides such as antimony oxide, tin oxide, titanium oxide, indium oxide, tin oxide-antimony oxide, etc.

Also, as the binder resin for the protective layer 5, there are polyamide resins, polyurethane resins, polyester resins, epoxy resins, polyketone resins, polycarbonate resins, polyvinylketone resins, polystyrene resins, polyacrylamide resins, etc.

The thickness of the protective layer 5 is generally from 0.5 to 20 μm, and preferably from 1 to 10 μm.

The electrophotographic photosensitive member of this invention can be used for a known electrophotographic image-forming process. That is, the photosensitive member can be used for an image forming process including the steps of uniformly charging the surface of a photosensitive member, applying an image exposure thereto to form electrostatic latent images, and developing the latent images by statically charged toner particles, and copy images having always stable image density can be obtained.

However, the electrophotographic photosensitive member of this invention is particularly suitably used for an image-forming process of forming images by a reversal development process as described below.

That is, the electrophotographic photosensitive member of this invention is particularly suitable for the image-forming process comprising uniformly negatively charging the surface of the electrophotographic photosensitive member, applying thereto an image exposure (electrophotographic exposing radiation) to form electrostatic latent images, attaching negatively charged toners to low-potential portions (exposed portions) of the electrostatic latent images to form toner images, superposing a transfer material on the electrophotographic photosensitive member carrying the toner images thus formed, and applying a positive charge to the photosensitive member from the back surface of the transfer material to transfer the toner images onto the transfer material.

Now, the new image-forming process to which the electrophotographic photosensitive member of this invention is applied will be explained.

As a means for uniformly charging the surface of the photosensitive member, a corona discharging device such as corotron, scorotron, di-corotron, pin-corotron, etc., or a charging roller can be used. The initial charging potential is preferably set in the range of from −700 volts to −200 volts.

As an image exposure means, an illuminating optical system composed of an illumination lamp and an image focusing optical system, a laser exposure optical system composed of a laser light generating source and a laser light deflection device, an LED array, a liquid crystal light bulb, a vacuum fluorescent tube array, an optical fiber array, a light wave guide array, etc., can be desirably used but the use of a light source emitting light having wavelengths in the spectral sensitive region of the photosensitive member is preferred.

The electrostatic latent images formed by the image exposure are developed using a developer to form toner images. As the developer, a two-component developer composed of carrier and toner or a one-component developer composed of toner only can be used. The toner particles may be magnetic toners containing a magnetic powder in the inside thereof or non-magnetic toners.

In the development, toner particles are allowed to approach the latent images or brought into device having a developer carrier containing the developer to attach the toner particles to the electrostatic latent images according to the potential of the latent images.

In this case, according to the charging polarity of the toners, the toners attach to low-potential portions (exposed portions) of the electrostatic latent images on the photosensitive member (negative development) or attach to high-potential portions (unexposed portions) of the electrostatic latent images (positive development). The developing mode can be practiced by selecting the charging polarity of toners being used. Since the electrophotographic photosensitive member of this invention has essentially a negatively charging property, toners of negatively charging property are selected in the case of the negative development and toners of positively charging property are selected in the case of the positive development.

During development, a bias voltage can be applied between the support of the electrophotographic photosensitive member and the developer carrier of the developing device. As the bias voltage, a direct current voltage or an alternating current voltage formed by overlapping direct current voltages. In particular, in the case of performing the negative development, it is necessary a bias voltage same as or lower in magnitude than the potential at the unexposed portions.

The toner images formed by the development can be transferred onto a transfer material by an optional method. As the transferring means, the aforesaid corona discharging device as well as a transfer roll, a press roll, etc., applied with a transfer voltage can be used but an electric field transfer performing the transfer by applying a charge to the photosensitive member from the back surface of the transfer material is effective. For example, in the case of negative charged toner particles of the toner images formed by the negative development, the toner images are suitably transferred onto the transfer material by applying positive corona discharging from the back surface of the transfer material.

After the transfer of the toner images is finished, the photosensitive member is, if necessary, cleaned to remove remaining toner images (untransferred toner images) and then the charges on the photosensitive member are discharged by means of an erase lump or a corotron for subsequent image forming step.

The electrophotographic photosensitive member of this invention can be suitably used in a so-called one pass multicolor image forming process.

For example, the electrophotographic photosensitive member can be suitably used for an image forming process by applying a first image exposure to form first electrostatic latent images, attaching negatively charged toners to low-potential portions of the first electrostatic latent images to form first toner images, then, applying second image exposure to form second electrostatic latent images, attaching positively charged second toners to high-potential portions of the second electrostatic latent images to form second toner images, after unifying the polarities of the first toner images and the second toner images to the polarity of one of both the toner images, superposing a transfer material on the electrophotographic photosensitive member carrying the first and second toner images, and applying a charge of an opposite polarity to the polarity of the first and second toner images from the back surface of the transfer material to transfer the first and second toner images onto the transfer material.

In the aforesaid one-pass multicolor image forming process, as a means for uniformly charging the photosensitive member, an image exposure means, a developing means, and a transferring means, the aforesaid means can be similarly used.

First, the surface of the photosensitive member is uniformly charged and then a first image exposure is applied. For the first image exposure, an image portion exposure for exposing the portions corresponding to image portions is employed. The first electrostatic latent images formed are developed using a first developer to form first toner images. In this case, negatively charged first toners are attached to low-potential portions (exposed portions) of the first electrostatic latent images using a developer carrier of a developing device applied with a bias voltage of a lower potential than the initially charged potential to form first toner images.

Then, a second image exposure is performed and for the second image exposure, a background portion exposure for exposing the portions corresponding to non-image portions is employed. In this case, it is preferred to use a light source the intensity of which is weaker than that of the light source used for the first image exposure and exposing so that the potential of the portions of the photosensitive member corresponding to the background portions reduces to almost a half of the initially charged potential employed as the light source for the second image exposure.

Then, positive charged second toners are attached to the portions not exposed in the second image exposure (the image portion in the second image exposure). In this case, it is preferred to perform the development by second toners carried on a developer carrier applied with a bias voltage of a higher potential than the potential of the portions of the photosensitive member corresponding to the background portions. Also, since the second development is a so-called overlapping development of applying the development onto the photosensitive member already having thereon the first toner images, it is preferred to use a two-component developer composed of a toner and a negatively charging low-density carrier at the second development for preventing the occurrence of the disturbance of the first toner images and the entrance of the first toners in the developed second toner. Also, a carrier having a density of less than 4.0 g/cm$^2$ is preferred.

After forming the first toner images and the second toner images on the photosensitive member, these toner images are transferred onto a transfer material. In this case, since these toners are charged in opposite polarities to each other, it is necessary unify these polarities to one of the polarities. For unifying the polarities, corona discharging by a charging device is applied before the transfer. In this case, since the electrophotographic photosensitive member of this invention has a negatively charging property, it is preferred to unify the polarities to a positive polarity. For charging before the transfer, it is preferred to use an alternating current voltage formed by overlapping positive direct current voltages.

Then, a transfer material is superposed on the toner images on the photosensitive member and a charging potential having a polarity opposite to the polarity of the toner images, e.g., of a negative polarity in the case of toner images unified to a positive polarity is applied to the photosensitive member from the back surface of the transfer material to transfer the toner images onto the transfer material. In this case, it is preferred to use a negative direct current voltage as the transfer potential.

The image forming is performed as described above in this invention and in this case, toners each having a different proper color can be used for the first and the second toners. For example, when the electrophotographic photosensitive member is a drum form, two-color images can be obtained during one rotation of the drum.

Then, the electrophotographic photosensitive member of this invention and the image forming process using it are described practically by the following examples.

EXAMPLE 1

The surface of an aluminum pipe of 40 mm in outer diameter and 319 mm in length subjected to mirror plane cutting was treated by buff polishing such that the surface roughness Ra became 0.17 μm. Then, a mixture having the following composition was prepared for forming an undercoating layer 4.

| | |
|---|---|
| Polyamide Resin (Luckermide 5003, trade name, made by Dainippon Ink and Chemicals, Inc.) | 1 part by weight |
| Methanol | 5 part by weight |
| n-Butanol | 3 part by weight |
| Water | 1 part by weight |

The aforesaid mixture was coated on the aluminum pipe by dip coating and dried for 10 minutes at 110° C. to form an undercoating layer 4 of 1 μm in thickness.

Then, a mixture of the following composition was prepared.

| | |
|---|---|
| X-Type Non-Metal Phthalocyanine (charge generating pigment) | 1 part by weight |
| Tetracyanoanthraquinodimethane Compound (Compound Ia-2) | 0.3 molar equivalent to the pigment |
| Polyvinyl Butyral Resin (BMl, trade name, made by Sekisui Chemical Co., Ltd.) | 1 part by weight |
| Cyclohexane | 60 part by weight |

The aforesaid mixture was dispersed for 10 minutes by a sand mill using glass beads of 1 mm in diameter to provide a dispersion of the pigment having a mean particle size of about 0.05 μm. The dispersion obtained was coated on the aforesaid undercoating layer by dip coating and dried by heating to 120° C. for 10 minutes to form a charge generating layer 1 of 0.25 μm in thickness.

Furthermore, a mixture of the following composition was prepared.

| | |
|---|---|
| N,N'-Diphenyl-N,N'-bis(3-methyl-phenyl)-[1,1'-biphenyl]-4,4'-diamine | 2 parts by weight |
| Polycarbonate Resin (bisphenol Z type) | 3 parts by weight |
| Monochlorobenzene | 20 parts by weight |

The aforesaid mixture was coated on the charge generating layer 1 by dip coating and dried for 60 minutes at 110° C. to form a charge transporting layer 2 of 20 μm in thickness.

The electrophotographic photosensitive member thus prepared was negatively charged using Scorotron (grid voltage: −300 volts), exposed to semiconductor laser (780 n.m. oscillation) to cause light decay, after exposure a probe of a surface potentiometer is placed on a position after 0.3 second (corresponding to the position after 0.6 second since charging), and the potential (VH) for nonexposure and the potential (VL: 30 erg/cm$^2$ exposure) for exposure were measured. Furthermore, Corotron (wire voltage: +5.0 KV) was disposed at the rear of the probe and the photosensitive member was positively charged. Thereafter, the charges are removed by a tungsten lamp.

In the system, the step of negative charging-exposure-positive charging-exposure for charge removal was defined as one cycle and the changes of VH and VL up to 200 cycles were measured. The measurement was carried out under the surrounding conditions of 32° C., 85% RH; 20° C., 55%RH; and 10° C., 15% RH. The results obtained are shown in Table 1.

Also, the electrophotographic photosensitive member described above was mounted on a laser printer (XP-11, trade name, made by Fuji Xerox Co., Ltd.). After continuously making 500 prints using A4 size (210 mm × 297 mm) papers, printing was carried out using B4 size (257 mm × 364 mm) papers only, and the density difference of printout between the A4 size paper portion and the widened portion by B4 size paper and the fog at the background portions in each portion were evaluated under the condition of 32° C., 85% RH. The results obtained are shown in Table 2.

In addition, in the laser printer, magnetic onecomponent toners of a negative polarity were used as the developer and also the toner images attached to the exposed portions of the photosensitive member were transferred by transfer Corotron of a DC voltage of +4.8 KV.

EXAMPLES 2 TO 7

By following the same procedure as Example 1 except that the amount of the tetracyanoanthraquinodimethane compound (Compound Ia-2) was changed to 0.005 molar equivalent (Example 2), 0.01 molar equivalent (Example 3), 0.1 molar equivalent (Example 4), 1.0 molar equivalent (Example 5), 2.0 molar equivalents (Example 6), or 4.0 molar equivalents (Example 7) to the pigment, electrophotographic photosensitive members were prepared and the same evaluations as above were made on each sample. The results obtained are shown in Table 1 and Table 2 below.

EXAMPLES 8 TO 44

By following the same procedure as Example 1 except that other compounds of formula (I) (i.e., the compounds of (Ia), (Ib), (Ic) or (Id)) shown in Tables 1 and 2 were used in place of the tetracyanoanthraquinodimethane compound (Ia-2) in the amounts shown in the tables, electrophotographic photosensitive materials were prepared and the same evaluations as above were made on each sample. The results obtained are shown in Table 1 and Table 2.

COMPARISON EXAMPLE 1

By following the same procedure as Example 1 except that the tetracyanoanthraquinodimethane compound was not added and the same evaluation was made. The results are shown in Table 1 and Table 2 below.

TABLE 1

| | No. | Amount (equivalent) | | 32° C., 85% RH at one cycle | at 200 cycles | 20° C., 55% RH at one cycle | at 200 cycles | (Unit: volt) 10° C., 15% RH at one cycle | at 200 cycles |
|---|---|---|---|---|---|---|---|---|---|
| | Tetracyanoanthraquino-dimethane compound (Ia) | | | | | | | | |
| Example 1 | Ia-2 | 0.3 | VH | −250 | −249 | −256 | −256 | −261 | −259 |
| | | | VL | −54 | −53 | −55 | −55 | −58 | −58 |
| Example 2 | Ia-2 | 0.005 | VH | −229 | −214 | −255 | −245 | −282 | −283 |
| | | | VL | −60 | −41 | −76 | −70 | −103 | −103 |
| Example 3 | Ia-2 | 0.01 | VH | −249 | −245 | −254 | −250 | −260 | −258 |
| | | | VL | −57 | −53 | −61 | −59 | −69 | −67 |
| Example 4 | Ia-2 | 0.1 | VH | −250 | −248 | −255 | −253 | −260 | −262 |
| | | | VL | −55 | −55 | −58 | −56 | −60 | −58 |
| Example 5 | Ia-2 | 1.0 | VH | −249 | −248 | −250 | −250 | −253 | −255 |
| | | | VL | −51 | −49 | −55 | −54 | −56 | −55 |
| Example 6 | Ia-2 | 2.0 | VH | −214 | −213 | −219 | −217 | −221 | −220 |
| | | | VL | −45 | −44 | −47 | −47 | −48 | −49 |
| Example 7 | Ia-2 | 4.0 | VH | −135 | −134 | −149 | −150 | −160 | −159 |
| | | | VL | −35 | −35 | −38 | −38 | −42 | −43 |
| Example 8 | Ia-3 | 0.3 | VH | −255 | −253 | −259 | −259 | −263 | −264 |
| | | | VL | −49 | −49 | −52 | −51 | −54 | −54 |
| Example 9 | Ia-5 | 0.3 | VH | −251 | −250 | −257 | −256 | −259 | −260 |
| | | | VL | −49 | −49 | −51 | −51 | −53 | −54 |
| Example 10 | Ia-6 | 0.3 | VH | −258 | −257 | −264 | −263 | −267 | −268 |
| | | | VL | −51 | −51 | −53 | −53 | −53 | −55 |
| Example 11 | Ia-8 | 0.3 | VH | −253 | −252 | −256 | −256 | −259 | −260 |
| | | | VL | −50 | −50 | −54 | −53 | −56 | −56 |
| | Anthraquinone Compound (Ib) | | | | | | | | |
| Example 12 | Ib-10 | 0.3 | VH | −256 | −254 | −257 | −257 | −258 | −259 |
| | | | VL | −55 | −53 | −56 | −56 | −58 | −59 |
| Example 13 | Ib-10 | 0.005 | VH | −232 | −217 | −251 | −244 | −280 | −283 |
| | | | VL | −62 | −39 | −74 | −70 | −102 | −104 |
| Example 14 | Ib-10 | 0.01 | VH | −249 | −245 | −254 | −250 | −260 | −261 |
| | | | VL | −59 | −53 | −59 | −57 | −64 | −66 |
| Example 15 | Ib-10 | 0.1 | VH | −253 | −252 | −256 | −256 | −257 | −258 |
| | | | VL | −57 | −56 | −59 | −58 | −60 | −61 |
| Example 16 | Ib-10 | 1.0 | VH | −249 | −248 | −251 | −251 | −253 | −253 |
| | | | VL | −52 | −51 | −53 | −53 | −53 | −54 |
| Example 17 | Ib-10 | 2.0 | VH | −223 | −221 | −226 | −225 | −229 | −230 |
| | | | VL | −49 | −48 | −50 | −50 | −51 | −52 |
| Example 18 | Ib-10 | 4.0 | VH | −150 | −148 | −154 | −153 | −157 | −158 |
| | | | VL | −41 | −40 | −43 | −43 | −44 | −45 |
| Example 19 | Ib-5 | 0.3 | VH | −257 | −256 | −258 | −257 | −258 | −260 |
| | | | VL | −51 | −50 | −54 | −53 | −54 | −55 |
| Example 20 | Ib-6 | 0.3 | VH | −263 | −261 | −264 | −264 | −265 | −267 |
| | | | VL | −50 | −49 | −53 | −51 | −54 | −56 |
| Example 21 | Ib-17 | 0.3 | VH | −260 | −259 | −260 | −260 | −264 | −264 |
| | | | VL | −53 | −52 | −54 | −55 | −54 | −57 |
| Example 22 | Ib-22 | 0.3 | VH | −263 | −261 | −265 | −263 | −269 | −267 |
| | | | VL | −55 | −53 | −57 | −56 | −58 | −58 |
| | Dicyanovinyl Compound (Ic) | | | | | | | | |
| Example 23 | Ic-11 | 0.3 | VH | −264 | −262 | −265 | −264 | −266 | −266 |
| | | | VL | −53 | −51 | −55 | −54 | −56 | −56 |
| Example 24 | Ic-11 | 0.005 | VH | −234 | −217 | −257 | −246 | −284 | −288 |
| | | | VL | −59 | −37 | −73 | −70 | −99 | −99 |
| Example 25 | Ic-11 | 0.01 | VH | −251 | −246 | −259 | −256 | −265 | −264 |
| | | | VL | −57 | −49 | −58 | −54 | −61 | −60 |
| Example 26 | Ic-11 | 0.1 | VH | −258 | −256 | −263 | −262 | −264 | −264 |
| | | | VL | −57 | −55 | −58 | −57 | −59 | −59 |
| Example 27 | Ic-11 | 1.0 | VH | −262 | −260 | −264 | −262 | −265 | −265 |
| | | | VL | −52 | −50 | −53 | −52 | −54 | −55 |
| Example 28 | Ic-11 | 2.0 | VH | −239 | −237 | −243 | −241 | −244 | −245 |
| | | | VL | −49 | −47 | −50 | −50 | −51 | −53 |
| Example 29 | Ic-11 | 4.0 | VH | −166 | −164 | −169 | −168 | −169 | −171 |
| | | | VL | −41 | −39 | −42 | −40 | −42 | −44 |
| Example 30 | Ic-1 | 0.3 | VH | −271 | −269 | −272 | −271 | −273 | −274 |
| | | | VL | −54 | −52 | −55 | −55 | −55 | −57 |

TABLE 1-continued

| | No. | Amount (equivalent) | | 32° C., 85% RH at one cycle | 32° C., 85% RH at 200 cycles | 20° C., 55% RH at one cycle | 20° C., 55% RH at 200 cycles | (Unit: volt) 10° C., 15% RH at one cycle | 10° C., 15% RH at 200 cycles |
|---|---|---|---|---|---|---|---|---|---|
| Example 31 | Ic-2 | 0.3 | VH | −266 | −266 | −267 | −268 | −267 | −269 |
| | | | VL | −52 | −51 | −53 | −52 | −53 | −55 |
| Example 32 | Ic-6 | 0.3 | VH | −278 | −276 | −280 | −278 | −281 | −281 |
| | | | VL | −58 | −57 | −59 | −58 | −58 | −61 |
| Example 33 | Ic-13 | 0.3 | VH | −270 | −269 | −273 | −271 | −275 | −276 |
| | | | VL | −55 | −54 | −56 | −54 | −55 | −57 |
| Quinon Compound (Id) | | | | | | | | | |
| Example 34 | Id-2 | 0.3 | VH | −263 | −262 | −265 | −265 | −265 | −267 |
| | | | VL | −55 | −54 | −56 | −57 | −56 | −58 |
| Example 35 | Id-2 | 0.005 | VH | −234 | −217 | −256 | −239 | −278 | −284 |
| | | | VL | −63 | −35 | −76 | −70 | −100 | −105 |
| Example 36 | Id-2 | 0.01 | VH | −249 | −245 | −253 | −251 | −257 | −256 |
| | | | VL | −59 | −57 | −62 | −61 | −64 | −65 |
| Example 37 | Id-2 | 0.1 | VH | −255 | −253 | −259 | −258 | −261 | −261 |
| | | | VL | −57 | −55 | −58 | −57 | −59 | −59 |
| Example 38 | Id-2 | 1.0 | VH | −259 | −257 | −262 | −262 | −263 | −265 |
| | | | VL | −53 | −52 | −54 | −54 | −55 | −57 |
| Example 39 | Id-2 | 2.0 | VH | −240 | −238 | −244 | −243 | −245 | −246 |
| | | | VL | −49 | −47 | −49 | −49 | −50 | −51 |
| Example 40 | Id-2 | 4.0 | VH | −171 | −168 | −177 | −176 | −179 | −180 |
| | | | VL | −38 | −36 | −39 | −38 | −40 | −40 |
| Example 41 | Id-1 | 0.3 | VH | −271 | −269 | −274 | −273 | −275 | −275 |
| | | | VL | −56 | −54 | −57 | −57 | −58 | −60 |
| Example 42 | Id-8 | 0.3 | VH | −280 | −277 | −281 | −279 | −281 | −280 |
| | | | VL | −61 | −59 | −63 | −61 | −63 | −62 |
| Example 43 | Id-11 | 0.3 | VH | −269 | −267 | −271 | −270 | −271 | −273 |
| | | | VL | −54 | −52 | −56 | −55 | −57 | −59 |
| Example 44 | Id-14 | 0.3 | VH | −258 | −257 | −259 | −259 | −261 | −263 |
| | | | VL | −51 | −49 | −52 | −52 | −52 | −54 |
| Comparison Example 1 | — | — | VH | −220 | −200 | −−254 | −245 | −290 | −300 |
| | | | VL | −65 | −30 | −82 | −75 | −110 | −114 |

TABLE 2

| | No. | Amount (equivalent) | Printout Density Difference Between the Portion Used for A-4 Size Paper and the Widened Portion | Fog at Background Position Portion Used for A-4 Size Paper | Fog at Background Position Widened Portion by B-4 Size Paper |
|---|---|---|---|---|---|
| | Tetracyanoanthraquino-dimethane compound (Ia) | | | | |
| Example 1 | Ia-2 | 0.3 | Uniform (no difference) | no fog | no fog |
| Example 2 | Ia-2 | 0.005 | * | no fog | fogged |
| Example 3 | Ia-2 | 0.01 | Uniform (no difference) | no fog | no fog |
| Example 4 | Ia-2 | 0.1 | " | no fog | no fog |
| Example 5 | Ia-2 | 1.0 | " | no fog | no fog |
| Example 6 | Ia-2 | 2.0 | " | fogged | fogged |
| Example 7 | Ia-2 | 4.0 | " | fogged | fogged |
| Example 8 | Ia-3 | 0.3 | " | no fog | no fog |
| Example 9 | Ia-5 | 0.3 | " | no fog | no fog |
| Example 10 | Ia-6 | 0.3 | " | no fog | no fog |
| Example 11 | Ia-8 | 0.3 | " | no fog | no fog |
| | Anthraqunone compound (Ib) | | | | |
| Example 12 | Ib-10 | 0.3 | Uniform (no difference) | no fog | no fog |
| Example 13 | Ib-10 | 0.005 | * | no fog | fogged |
| Example 14 | Ib-10 | 0.01 | Uniform (no difference) | no fog | no fog |
| Example 15 | Ib-10 | 0.1 | " | no fog | no fog |
| Example 16 | Ib-10 | 1.0 | " | no fog | no fog |
| Example 17 | Ib-10 | 2.0 | " | no fog | no fog |
| Example 18 | Ib-10 | 4.0 | " | fogged | fogged |
| Example 19 | Ib-5 | 0.3 | " | no fog | no fog |
| Example 20 | Ib-6 | 0.3 | " | no fog | no fog |
| Example 21 | Ib-17 | 0.3 | " | no fog | no fog |
| Example 22 | Ib-22 | 0.3 | " | no fog | no fog |
| | Dicyanovinyl compound (Ic) | | | | |
| Example 23 | Ic-11 | 0.3 | Uniform (no difference) | no fog | no fog |
| Example 24 | Ic-11 | 0.005 | * | no fog | fogged |
| Example 25 | Ic-11 | 0.01 | Uniform (no difference) | no fog | no fog |
| Example 26 | Ic-11 | 0.1 | " | no fog | no fog |
| Example 27 | Ic-11 | 1.0 | " | no fog | no fog |
| Example 28 | Ic-11 | 2.0 | " | no fog | no fog |
| Example 29 | Ic-11 | 4.0 | " | fogged | fogged |
| Example 30 | Ic-1 | 0.3 | " | no fog | no fog |
| Example 31 | Ic-2 | 0.3 | " | no fog | no fog |
| Example 32 | Ic-6 | 0.3 | " | no fog | no fog |
| Example 33 | Ic-13 | 0.3 | " | no fog | no fog |
| | Quinone compound (Id) | | | | |

TABLE 2-continued

| | No. | Amount (equivalent) | Printout Density Difference Between the Portion Used for A-4 Size Paper and the Widened Portion | Fog at Background Position Portion Used for A-4 Size Paper | Widened Portion by B-4 Size Paper |
|---|---|---|---|---|---|
| Example 34 | Id-2 | 0.3 | Uniform (no difference) | no fog | no fog |
| Example 35 | Id-2 | 0.005 | * | no fog | fogged |
| Example 36 | Id-2 | 0.01 | Uniform (no difference) | no fog | no fog |
| Example 37 | Id-2 | 0.1 | " | no fog | no fog |
| Example 38 | Id-2 | 1.0 | " | no fog | no fog |
| Example 39 | Id-2 | 2.0 | " | no fog | no fog |
| Example 40 | Id-2 | 4.0 | " | fogged | fogged |
| Example 41 | Id-1 | 0.3 | " | no fog | no fog |
| Example 42 | Id-8 | 0.3 | " | no fog | no fog |
| Example 43 | Id-11 | 0.3 | " | no fog | no fog |
| Example 44 | Id-14 | 0.3 | " | no fog | no gog |
| Comparison Example 1 | — | — | | no fog | fogged |

*The printout density in the widened portion was higher than that in the portion used for A-4 size paper.

EXAMPLES 45 TO 68

By following the same procedure as Example 1 except that the X-type non-metal phthalocyanine and the tetracyanoanthraquinodimethane compound in Example 1 were changed to the compounds shown in Table 3 below, electrophotographic photosensitive members were prepared and the same evaluations were made on each sample. The results obtained are shown in Table 3 and Table 4 below.

COMPARISON EXAMPLES 2 TO 7

By following the same procedures as Examples 45 to 50 except that the tetracyanoanthraquinodimethane compound was not added, electrophotographic photosensitive members were prepared and the same evaluations were made on each sample. The results are shown in Table 3 and Table 4.

TABLE 3

| | Charge Generating Pigment | No. | Amount (equivalent) | 32° C., 85% RH at one cycle | 32° C., 85% RH at 200 cycles | 20° C., 55% RH at one cycle | 20° C., 55% RH at 200 cycles | 10° C., 15% RH at one cycle | 10° C., 15% RH at 200 cycles |
|---|---|---|---|---|---|---|---|---|---|
| | | Tetracyanoanthraquinodimethane compound (Ia) | | | | | | | |
| Example 45 | II-3 | Ia-1 | 0.3 | VH −289 VL −74 | −288 −74 | −291 −76 | −291 −75 | −292 −77 | −293 −78 |
| Example 46 | II-6 | Ia-7 | 0.3 | VH −283 VL −71 | −281 −71 | −286 −74 | −285 −73 | −286 −75 | −286 −75 |
| Example 47 | II-10 | Ia-10 | 0.3 | VH −287 VL −77 | −286 −77 | −290 −79 | −288 −78 | −292 −80 | −292 −81 |
| Example 48 | II-12 | Ia-11 | 0.3 | VH −284 VL −94 | −282 −94 | −286 −98 | −286 −99 | −289 −101 | −290 −102 |
| Example 49 | II-20 | Ia-19 | 0.3 | VH −283 VL −77 | −282 −77 | −285 −80 | −286 −79 | −288 −82 | −289 −83 |
| Example 50 | Vanadyl-phthalocyanine | Ia-22 | 0.3 | VH −243 VL −49 | −243 −48 | −247 −50 | −246 −50 | −249 −52 | −250 −52 |
| | | Anthraquinon compound (Ib) | | | | | | | |
| Example 51 | II-3 | Ib-3 | 0.3 | VH −289 VL −74 | −287 −72 | −290 −76 | −290 −75 | −291 −76 | −293 −79 |
| Example 52 | II-6 | Ib-12 | 0.3 | VH −285 VL −72 | −284 −71 | −286 −73 | −286 −73 | −286 −73 | −287 −74 |
| Example 53 | II-10 | Ib-13 | 0.3 | VH −288 VL −78 | −287 −77 | −290 −79 | −291 −79 | −291 −80 | −294 −83 |
| Example 54 | II-12 | Ib-16 | 0.3 | VH −289 VL −93 | −288 −92 | −293 −99 | −291 −99 | −294 −101 | −294 −102 |
| Example 55 | II-20 | Ib-19 | 0.3 | VH −285 VL −71 | −284 −70 | −289 −73 | −287 −73 | −290 −75 | −291 −76 |
| Example 56 | Vanadyl-phthalocyanine | Ib-23 | 0.3 | VH −248 VL −49 | −246 −48 | −251 −52 | −250 −52 | −253 −54 | −252 −52 |
| | | Dicyanovinyl compound (Ic) | | | | | | | |
| Example 57 | II-3 | Ic-3 | 0.3 | VH −281 VL −76 | −279 −75 | −283 −78 | −280 −78 | −284 −78 | −284 −81 |
| Example 58 | II-6 | Ic-7 | 0.3 | VH −284 VL −79 | −282 −77 | −285 −80 | −284 −79 | −287 −81 | −287 −80 |
| Example 59 | II-10 | Ic-10 | 0.3 | VH −281 VL −74 | −280 −73 | −282 −75 | −282 −75 | −281 −75 | −283 −77 |
| Example 60 | II-12 | Ic-16 | 0.3 | VH −289 VL −91 | −287 −90 | −291 −94 | −290 −93 | −292 −94 | −292 −96 |
| Example 61 | II-20 | Ic-17 | 0.3 | VH −279 VL −72 | −278 −70 | −282 −74 | −282 −73 | −283 −73 | −285 −75 |
| Example 62 | Vanadyl-phthalocyanine | Ic-23 | 0.3 | VH −251 VL −51 | −250 −49 | −254 −54 | −253 −53 | −257 −55 | −256 −54 |

TABLE 3-continued (Unit: Volt)

| | Charge Generating Pigment | No. | Amount (equivalent) | | 32° C., 85% RH at one cycle | at 200 cycles | 20° C., 55% RH at one cycle | at 200 cycles | 10° C., 15% RH at one cycle | at 200 cycles |
|---|---|---|---|---|---|---|---|---|---|---|
| | | | | Quinon compound (Id) | | | | | | |
| Example 63 | II-3 | Id-3 | 0.3 | VH | −280 | −278 | −284 | −282 | −286 | −286 |
| | | | | VL | −76 | −74 | −78 | −77 | −78 | −80 |
| Example 64 | II-6 | Id-5 | 0.3 | VH | −285 | −283 | −286 | −285 | −287 | −285 |
| | | | | VL | −80 | −78 | −80 | −79 | −81 | −80 |
| Example 65 | II-10 | Id-7 | 0.3 | VH | −286 | −285 | −287 | −287 | −288 | −289 |
| | | | | VL | −81 | −79 | −82 | −82 | −83 | −84 |
| Example 66 | II-12 | Id-18 | 0.3 | VH | −291 | −289 | −292 | −292 | −292 | −294 |
| | | | | VL | −94 | −93 | −95 | −96 | −97 | −99 |
| Example 67 | II-20 | Id-20 | 0.3 | VH | −279 | −278 | −281 | −281 | −283 | −282 |
| | | | | VL | −71 | −69 | −73 | −73 | −74 | −74 |
| Example 68 | Vanadyl-phthalocyanine | Id-24 | 0.3 | VH | −249 | −247 | −253 | −253 | −256 | −258 |
| | | | | VL | −47 | −45 | −49 | −50 | −51 | −53 |
| Comparison Example 2 | II-3 | — | — | VH | −267 | −241 | −290 | −282 | −301 | −303 |
| | | | | VL | −92 | −61 | −110 | −101 | −135 | −148 |
| Comparison Example 3 | II-6 | — | — | VH | −256 | −243 | −286 | −279 | −298 | −301 |
| | | | | VL | −89 | −58 | −107 | −98 | −131 | −139 |
| Comparison Example 4 | II-10 | — | — | VH | −261 | −239 | −291 | −294 | −300 | −305 |
| | | | | VL | −99 | −60 | −113 | −99 | −137 | −149 |
| Comparison Example 5 | II-12 | — | — | VH | −279 | −261 | −291 | −285 | −300 | −306 |
| | | | | VL | −121 | −101 | −133 | −121 | −152 | −164 |
| Comparison Example 6 | II-20 | — | — | VH | −253 | −228 | −286 | −277 | −298 | −307 |
| | | | | VL | −92 | −66 | −114 | −109 | −137 | −149 |
| Comparison Example 7 | Vanadyl-phthalocyanine | — | — | VH | −221 | −190 | −245 | −238 | −277 | −282 |
| | | | | VL | −55 | −30 | −63 | −58 | −96 | −100 |

TABLE 4

| | Charge Generating Pigment | No. | Amount (equivalent) | Printout Density Difference Between the Portion Used for A-4 Size Paper and the Widened Portion | Fog at Background Position Portion Used for A-4 Size Paper | Widened Portion by B-4 Size Paper |
|---|---|---|---|---|---|---|
| | | | Tetracyanoanthraquinodimethane compound (Ia) | | | |
| Example 45 | II-3 | Ia-1 | 0.3 | Uniform (no difference) | no fog | no fog |
| Example 46 | II-7 | Ia-7 | 0.3 | " | no fog | no fog |
| Example 47 | II-10 | Ia-10 | 0.3 | " | no fog | no fog |
| Example 48 | II-12 | Ia-11 | 0.3 | " | no fog | no fog |
| Example 49 | II-20 | Ia-19 | 0.3 | " | no fog | no fog |
| Example 50 | Vanadyl-phthalocyanine | Ia-22 | 0.3 | " | no fog | no fog |
| | | | Anthraquinon compound (Ib) | | | |
| Example 51 | II-3 | Ib-1 | 0.3 | " | no fog | no fog |
| Example 52 | II-6 | Ib-7 | 0.3 | " | no fog | no fog |
| Example 53 | II-10 | Ib-10 | 0.3 | " | no fog | no fog |
| Example 54 | II-12 | Ib-11 | 0.3 | " | no fog | no fog |
| Example 55 | II-20 | Ib-19 | 0.3 | " | no fog | no fog |
| Example 56 | Vanadyl-phthalocyanine | Ib-22 | 0.3 | " | no fog | no fog |
| | | | Dicyanovinyl compound (Ic) | | | |
| Example 57 | II-3 | Ic-3 | 0.3 | " | no fog | no fog |
| Example 58 | II-6 | Ic-7 | 0.3 | " | no fog | no fog |
| Example 59 | II-10 | Ic-10 | 0.3 | " | no fog | no fog |
| Example 60 | II-12 | Ic-16 | 0.3 | " | no fog | no fog |
| Example 61 | II-20 | Ic-17 | 0.3 | " | no fog | no fog |
| Example 62 | Vanadyl-phthalocyanine | Ic-23 | 0.3 | " | no fog | no fog |
| | | | Quinon compound (Id) | | | |
| Example 63 | II-3 | Id-3 | 0.3 | " | no fog | no fog |
| Example 64 | II-6 | Id-5 | 0.3 | " | no fog | no fog |
| Example 65 | II-10 | Id-7 | 0.3 | " | no fog | no fog |
| Example 66 | II-12 | Id-18 | 0.3 | " | no fog | no fog |
| Example 67 | II-20 | Id-20 | 0.3 | " | no fog | no fog |
| Example 68 | Vanadyl-phthalocyanine | Id-24 | 0.3 | " | no fog | no fog |
| Comparison Example 2 | II-3 | — | — | " | no fog | fogged |
| Comparison Example 3 | II-6 | — | — | " | no fog | fogged |
| Comparison Example 4 | II-10 | — | — | " | no fog | fogged |
| Comparison Example 5 | II-12 | — | — | " | no fog | fogged |

TABLE 4-continued

| | Charge Generating Pigment | No. | Amount (equivalent) | Printout Density Difference Between the Portion Used for A-4 Size Paper and the Widened Portion | Fog at Background Position | |
|---|---|---|---|---|---|---|
| | | | | | Portion Used for A-4 Size Paper | Widened Portion by B-4 Size Paper |
| Comparison Example 6 | II-20 | — | — | " | no fog | fogged |
| Comparison Example 7 | Vanadyl-phthalocyanine | — | — | " | no fog | fogged |

*Same as that defined in Table 2.

EXAMPLES 69 TO 96

By following the same procedure as Example 1 except that an aluminum pipe of 84 mm in outside diameter and 310 mm in length subjected to mirror plane cutting was used as the substrate, the perylene pigment (Compound IV-1) was used as the charge generating pigment, and each of the compounds shown in Table 5 was used as the compound of formula (I), electrophotographic photosensitive members were prepared.

Each of the electrophotographic photosensitive members was negatively charged using Scorotron (grid voltage: −300 volts), exposed to a halogen lamp (using an interference filter of 550 n.m. as the center wavelength) to cause light decay, after exposure, a proble of a surface densitometer was placed on the position after 0.3 second (corresponding to the position after 0.6 second since charging), and the potential (VH) for nonexposure and the potential (VL: 30 erg/cm² exposure) for exposure were measured.

Furthermore, Corotron (wire voltage: +5.0 KV) was disposed at the rear of the probe, the photosensitive member was positive charged, and thereafter the charges were removed by a tungsten lamp. In the system, the step of negative charging-exposure-positive charging-exposure for charge removal was defined as one cycle and the changes of VH and VL upto 200 cycles were measured. The measurement was performed under the surrounding conditions of 32° C., 85% RH, 20° C., 55% RH, and 10° C., 15% RH. The results obtained are shown in Table 5 below.

COMPARISON EXAMPLE 8

By following the same procedure as Example 69 except that the dicyanovinyl compound was not added, an electrophotographic photosensitive member was prepared and the same evaluations were made. The results are shown in Table 5.

COMPARISON EXAMPLES 9 AND 10

By following the same procedure as Example 69 except that dibromoanthanthrone or the bisazo pigment shown by the following structural formula

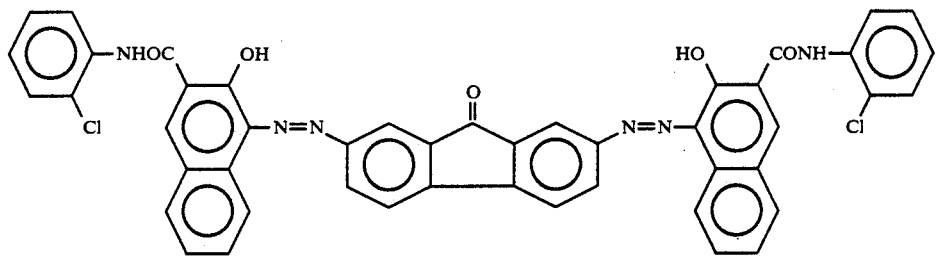

was used in place of the perylene pigment (Compound IV-1), electrophotographic photosensitive members were prepared and the same evaluations were made on each sample. The results are shown in Table 5 below.

COMPARISON EXAMPLES 11 TO 16

By following the same procedures as Comparison Examples 9 and 10 except that the compound of formula (Ib), (Ic) or (Id) shown in Table 5 was used in place of the tetracyanoanthra-quinodimethane compound of formula (Ia), electrophotographic photosensitive members were prepared and the same evaluations were made on each sample. The results are shown in Table 5.

COMPARISON EXAMPLES 17 AND 18

By following the same procedures as Comparison Examples 9 and 10 except that the tetracyanoanthraquinodimethane compound of formula (Ia) was not added, electrophotographic photosensitive members were prepared and the evaluations were made on each sample. The results are shown in Table 5.

TABLE 5

| | Charge Generating Pigment | No. | Amount (equivalent) | 32° C., 85% RH | | 20° C., 55% RH | | 10° C., 15% RH (Unit: Volt) | |
|---|---|---|---|---|---|---|---|---|---|
| | | | | at one cycle | at 200 cycles | at one cycle | at 200 cycles | at one cycle | at 200 cycles |
| | | Tetracyanoanthra-quinodimethane compound (Ia) | | | | | | | |
| Example 69 | IV-1 | Ia-9 | 0.3 | VH −271 | −271 | −275 | −274 | −279 | −280 |
| | | | | VL −151 | −152 | −154 | −153 | −155 | −156 |
| Example 70 | IV-1 | Ia-12 | 0.3 | VH −283 | −281 | −284 | −284 | −285 | −286 |

TABLE 5-continued

| | Charge Generating Pigment | No. | Amount (equivalent) | | 32° C., 85% RH at one cycle | at 200 cycles | 20° C., 55% RH at one cycle | at 200 cycles | 10° C., 15% RH at one cycle | (Unit: Volt) at 200 cycles |
|---|---|---|---|---|---|---|---|---|---|---|
| | | | | VL | −158 | −157 | −160 | −159 | −161 | −161 |
| Example 71 | IV-1 | Ia-14 | 0.3 | VH | −270 | −269 | −276 | −274 | −279 | −280 |
| | | | | VL | −140 | −148 | −152 | −151 | −153 | −153 |
| Example 72 | IV-1 | Ia-16 | 0.3 | VH | −285 | −283 | −290 | −290 | −290 | −289 |
| | | | | VL | −515 | −153 | −158 | −159 | −160 |
| Example 73 | IV-1 | Ia-17 | 0.3 | VH | −281 | −280 | −284 | −282 | −286 | −286 |
| | | | | VL | −153 | −152 | −155 | −153 | −155 | −156 |
| Example 74 | IV-1 | Ia-18 | 0.3 | VH | −270 | −270 | −272 | −273 | −275 | −277 |
| | | | | VL | −145 | −145 | −147 | −147 | −148 | −147 |
| Example 75 | IV-1 | Ia-21 | 0.3 | VH | −281 | −280 | −283 | −281 | −284 | −283 |
| | | | | VL | −151 | −150 | −153 | −152 | −155 | −155 |
| Comparison Example 8 | IV-1 | — | — | VH | −271 | −253 | −282 | −273 | −299 | −297 |
| | | | | VL | −166 | −131 | −179 | −171 | −208 | −210 |
| Comparison Example 9 | Dibromo-anthanthrone | Ia-9 | 0.3 | VH | −270 | −253 | −298 | −291 | −299 | −297 |
| | | | | VL | −145 | −132 | −170 | −162 | −181 | −180 |
| Comparison Example 10 | | Ia-9 | 0.3 | VH | −229 | −221 | −285 | −271 | −291 | −287 |
| | | | | VL | −68 | −49 | −80 | −64 | −109 | −110 |
| | Anthraquinon compound (Ib) | | | | | | | | | |
| Example 76 | IV-1 | Ib-9 | 0.3 | VH | −280 | −279 | −281 | −280 | −284 | −282 |
| | | | | VL | −157 | −157 | −160 | −160 | −163 | −163 |
| Example 77 | IV-1 | Ib-4 | 0.3 | VH | −290 | −288 | −291 | −290 | −291 | −293 |
| | | | | VL | −163 | −161 | −165 | −164 | −165 | −168 |
| Example 78 | IV-1 | Ib-8 | 0.3 | VH | −280 | −280 | −284 | −282 | −284 | −287 |
| | | | | VL | −159 | −157 | −161 | −160 | −161 | −164 |
| Example 79 | IV-1 | Ib-14 | 0.3 | VH | −289 | −287 | −290 | −290 | −291 | −290 |
| | | | | VL | −161 | −159 | −163 | −162 | −164 | −163 |
| Example 80 | IV-1 | Ib-15 | 0.3 | VH | −287 | −286 | −288 | −287 | −287 | −290 |
| | | | | VL | −156 | −155 | −156 | −156 | −157 | −159 |
| Example 81 | IV-1 | Ib-18 | 0.3 | VH | −280 | −278 | −281 | −281 | −283 | −281 |
| | | | | VL | −149 | −148 | −152 | −152 | −153 | −152 |
| Example 82 | IV-1 | Ib-21 | 0.3 | VH | −286 | −284 | −288 | −287 | −289 | −292 |
| | | | | VL | −154 | −153 | −155 | −155 | −157 | −160 |
| Comparison Example 11 | Dibromo-anthanthrone | Ib-9 | 0.3 | VH | −271 | −253 | −299 | −291 | −300 | −294 |
| | | | | VL | −143 | −130 | −170 | −165 | −190 | −186 |
| Comparison Example 12 | | Ib-9 | 0.3 | VH | −240 | −230 | −288 | −275 | −290 | −284 |
| | | | | VL | −71 | −48 | −81 | −63 | −108 | −106 |
| | Dicyanovinyl compound (Ic) | | | | | | | | | |
| Example 83 | IV-1 | Ic-8 | 0.3 | VH | −275 | −273 | −278 | −277 | −278 | −281 |
| | | | | VL | −159 | −157 | −163 | −162 | −163 | −165 |
| Example 84 | IV-1 | Ic-5 | 0.3 | VH | −281 | −278 | −283 | −281 | −285 | −285 |
| | | | | VL | −163 | −161 | −166 | −164 | −167 | −168 |
| Example 85 | IV-1 | Ic-9 | 0.3 | VH | −289 | −286 | −292 | −291 | −293 | −292 |
| | | | | VL | −171 | −170 | −174 | −174 | −175 | −176 |
| Example 86 | IV-1 | Ic-14 | 0.3 | VH | −280 | −277 | −284 | −282 | −285 | −282 |
| | | | | VL | −173 | −170 | −176 | −173 | −178 | −175 |
| Example 87 | IV-1 | Ic-15 | 0.3 | VH | −276 | −274 | −279 | −279 | −278 | −281 |
| | | | | VL | −169 | −166 | −171 | −172 | −172 | −175 |
| Example 88 | IV-1 | Ic-20 | 0.3 | VH | −286 | −283 | −288 | −289 | −290 | −293 |
| | | | | VL | −175 | −173 | −175 | −176 | −175 | −179 |
| Example 89 | IV-1 | Ic-22 | 0.3 | VH | −269 | −268 | −271 | −270 | −272 | −272 |
| | | | | VL | −158 | −157 | −159 | −159 | −159 | −160 |
| Comparison Example 13 | Dibromo-anthanthrone | Ic-8 | 0.3 | VH | −273 | −251 | −301 | −291 | −299 | −294 |
| | | | | VL | −151 | −134 | −169 | −158 | −193 | −194 |
| Comparison Example 14 | | Ic-8 | 0.3 | VH | −239 | −227 | −284 | −271 | −291 | −285 |
| | | | | VL | −69 | −39 | −81 | −73 | −103 | −104 |
| | Quinon compound (Id) | | | | | | | | | |
| Example 90 | IV-1 | Id-6 | 0.3 | VH | −273 | −271 | −275 | −275 | −276 | −279 |
| | | | | VL | −153 | −152 | −155 | −156 | −159 | −162 |
| Example 91 | IV-1 | Id-9 | 0.3 | VH | −284 | −282 | −285 | −284 | −286 | −284 |
| | | | | VL | −158 | −156 | −159 | −158 | −162 | −160 |
| Example 92 | IV-1 | Id-10 | 0.3 | VH | −289 | −287 | −291 | −290 | −291 | −293 |
| | | | | VL | −161 | −159 | −162 | −162 | −162 | −164 |
| Example 93 | IV-1 | Id-13 | 0.3 | VH | −270 | −266 | −271 | −270 | −272 | −272 |
| | | | | VL | −149 | −146 | −151 | −151 | −153 | −154 |
| Example 94 | IV-1 | Id-16 | 0.3 | VH | −276 | −274 | −278 | −276 | −281 | −277 |
| | | | | VL | −156 | −153 | −158 | −156 | −161 | −160 |
| Example 95 | IV-1 | Id-17 | 0.3 | VH | −284 | −283 | −285 | −286 | −286 | −290 |
| | | | | VL | −159 | −159 | −161 | −163 | −165 | −167 |
| Example 96 | IV-1 | Id-22 | 0.3 | VH | −271 | −269 | −272 | −272 | −272 | −273 |
| | | | | VL | −151 | −150 | −152 | −152 | −153 | −154 |
| Comparison Example 15 | Dibromo-anthanthrone | Id-6 | 0.3 | VH | −276 | −254 | −298 | −296 | −299 | −294 |
| | | | | VL | −144 | −131 | −165 | −161 | −185 | −191 |
| Comparison Example 16 | | Id-6 | 0.3 | VH | −239 | −231 | −280 | −270 | −282 | −284 |
| | | | | VL | −71 | −39 | −79 | −70 | −91 | −93 |
| Comparison | Dibromo- | — | — | VH | −271 | −252 | −298 | −295 | −301 | −284 |

TABLE 5-continued

|  | Charge Generating Pigment | No. | Amount (equivalent) | 32° C., 85% RH | | 20° C., 55% RH | | (Unit: Volt) 10° C., 15% RH | |
|---|---|---|---|---|---|---|---|---|---|
|  |  |  |  | at one cycle | at 200 cycles | at one cycle | at 200 cycles | at one cycle | at 200 cycles |
| Example 17 | anthanthrone |  |  | VL −147 | −135 | −170 | −165 | −191 | −198 |
| Comparison | | — | — | VH −249 | −238 | −290 | −277 | −294 | −289 |
| Example 18 | | | | VL −75 | −43 | −85 | −71 | −113 | −121 |

EXAMPLES 97 TO 100 AND COMPARISON EXAMPLE 19

Each of the electrophotographic photosensitive members prepared in Examples 1, 12, 23, and 34 and Comparison Example 1 was negatively charged using Scorotron (grid voltage: −300 volts), image-exposed by semiconductor laser (780 n.m. oscillation) to cause light decay, after exposure, a probe of a surface potentiometer was placed on the portion after 0.3 second (corresponding to the place after 0.6 second since charging), and the potential (VH) for nonexposure and the potential (VL: 20 erg/cm² exposure) for exposure were measured. Furthermore, Corotron (wire voltage: −5.0 KV) was disposed at the rear of the probe to negatively charge the photosensitive member and thereafter, the charges were removed by tungsten lamp. In the system, the step of negative charging-exposure-negative charging-exposure for charge removal was defined as one cycle and the changes of VH and VL up to 200 cycles were measured. The measurement was performed under the surrounding conditions of 32° C., 85% RH, 20° C., 55% RH, and 10° C., 15% RH. The results are shown in Table 6 below.

made by Fuji Xerox Co.), 500 prints of red and black patterns were made using B4 size papers, and the changes of the printout densities at the red portions and the black portions were observed.

In the electrophotographic photosensitive members of Examples 101 to 104, clear printouts having red portions and black portions without no fog at the background portion were obtained but in the electrophotographic photosensitive members of Comparison Example 20, the fog of the red toners at the background portions was increased the red printout became broader, and black printout became thinner with the increase of the number of the printed papers.

As described above, the electrophotographic photosensitive member of this invention has the charge generating layer containing the charge generating pigment having the positive hole transporting property and the compound of formula (I) [e.g., at least one of the compounds shown by formulae (Ia), (Ib), (Ic), and (Id)] and has the excellent effects that the sensitivity is improved, the charging property is good, the photosensitivity and the charging potential are stable to the changes of surrounding conditions, and the potentials of the exposed portions and unexposed portions are stable without

TABLE 6

|  | Charge Generating Pigment | Compound of Formula (I) | | 32° C., 85% RH | | 20° C., 55% RH | | 10° C., 15% RH | |
|---|---|---|---|---|---|---|---|---|---|
|  |  | No. | Amount (equivalent) | at one cycle | at 200 cycles | at one cycle | at 200 cycles | at one cycle | at 200 cycles |
| Example 97 | X-Type Non-Metal Phthalocyanine | Ia-2 | 0.3 | VH −251 VL −57 | −251 −57 | −253 −59 | −252 −58 | −256 −61 | −256 −62 |
| Example 98 | X-Type Non-Metal Phthalocyanine | Ib-10 | 0.3 | VH −251 VL −58 | −250 −56 | −253 −59 | −251 −59 | −253 −61 | −256 −62 |
| Example 99 | X-Type Non-Metal Phthalocyanine | Ic-11 | 0.3 | VH −251 VL −61 | −248 −58 | −253 −62 | −252 −61 | −255 −62 | −256 −64 |
| Example 100 | X-Type Non-Metal Phthalocyanine | Id-2 | 0.3 | VH −253 VL −61 | −251 −59 | −255 −63 | −255 −63 | −255 −63 | −257 −64 |
| Comparison Example 19 | X-Type Non-Metal Phthalocyanine | — | — | VH −226 VL −69 | −211 −62 | −257 −88 | −251 −82 | −292 −117 | −299 −120 |

EXAMPLES 101 TO 104 AND COMPARISON EXAMPLE 20

An aluminum pipe of 85 mm in outside diameter and 310 mm in length subjected to mirror-plane cutting was surface-polished by grinding stone so that the surface roughness Ra became 0.15 μm. Then, by following the same procedures as Examples 1, 12, 23, and 34 and Comparison Examples 1 to 4 using the aluminum pipe as the substrate, electrophotographic photosensitive members were prepared.

Each of the electrophotographic photosensitive members thus prepared was mounted on a two-color laser printer (operated by repeating the steps of charging, 1st laser exposure, negative-charging red toner development of the unexposed portions, 2nd laser exposure, positive-charging black toner development of the unexposed portions, charging before transfer by AC formed by overlapping DC, transferring by negative DC corotron, cleaning, and charge removal) produced by improving a copying machine (FX 2700, trade name, being reduced during making many copies as compared to the case of containing no such components.

The electrophotographic photosensitive member of this invention is particularly suitably applied to the electrophotographic image forming process comprising the repeating steps of uniform charging, image exposure, reversal development, positive charging transfer, and charge dismissal, e.g., the case of using a laser printer, etc., and in this case, the surface density of the photosensitive member in the image exposure always keeps the stable potential without causing the reduction in potential with a repeated image-forming operation from the initial image forming step after repeating many times the image forming step, and hence images having stable image density can be obtained in continuous repeated use and also the formation of fog can be restrained in such a case.

Furthermore, in the case of changing the size of transfer papers to a large size of papers after repeating many times the image forming operation, the increase of the transfer density at the broadened portions of the new transfer papers and hence images having a uniform density without fog at the background portions can be obtained.

In addition, when the compound of formula (I) is not contained in the charge generating layer 1, the potential of the exposed portions and the unexposed portions is gradually reduced with the repeating operation of the image-forming step, the image density is gradually increased and fog forms at the background portions. Also, in the case of changing the size of transfer papers to a large size paper after repeating many times the image forming step, the increase of image density and the formation of background fog are observed at the broadened portions of the new transfer papers.

Furthermore, the electrophotographic photosensitive member of this invention can be applied to a so-called one-pass multicolor image forming process.

While the invention has been described in detail and with reference to specific embodiments thereof, it will be apparent to one skilled in the art that various changes and modifications can be made therein without departing from the spirit and scope thereof.

What is claimed is:

1. An electrophotographic photosensitive member having a charge generating layer and a charge transporting layer successively formed on a support, wherein the charge generating layer contains a charge generating pigment having a hole transporting property and at least one of the compounds represented by following formulae (Ia), (Ic), and (Id) in a binder resin;

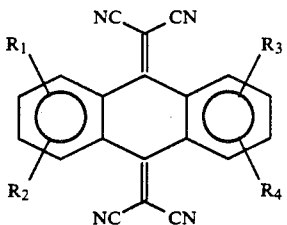

wherein $R_1$, $R_2$, $R_3$, and $R_4$ each represents a hydrogen atom, an alkyl group, an alkoxycarbonyl group, a halogen atom, an alkyl-substituted amino group, a hydroxy group, an aryl group, a nitro group, a cyano group, a carboxyalkyl group, an aralkyl group, an alkoxy group, an aryloxy group, an aralkyloxy group, a carboxyaryl group, a carboxyaralkyl group, an aryloxycarbonyl group, or an aralkyloxycarbonyl group;

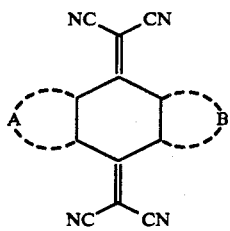

wherein A and B each represents a group of forming a ring shown by formula (1), (2) or (3) below, provided that at least one of A and B represents a group necessary for forming the ring shown by formula (1) or (2)

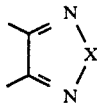

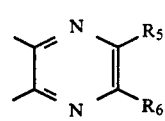

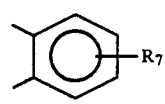

wherein X represents a selenium atom or a sulfur atom; $R_5$ and $R_6$ each represents a hydrogen atom, an alkyl group, an aryl group, an alkoxycarbonyl group, or an arylcarbonyl group; and $R_7$ represents a hydrogen atom, an alkyl group, a halogen atom, an aryl group, an alkoxy group, an aryloxy group, an alkoxycarbonyl group, an arylcarbonyl group, a nitro group, a cyano group, or a benzyloxy group; and

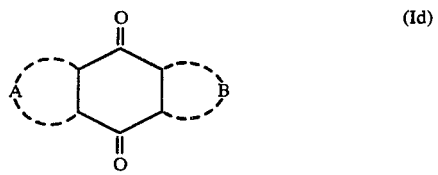

wherein A and B are as defined on the compound of formula (Ic).

2. The electrophotographic photosensitive member as in claim 1, wherein at least one of the compounds shown by formulae (Ia), (Ic), and (Id) is incorporated in the charge generating layer in an amount of from 0.01 to 2 molar equivalents to the charge generating pigment having the positive hole transporting property.

3. The electrophotographic photosensitive member as in claim 1, wherein the charge generating pigment having the positive hole transporting property is a phthalocyanine series pigment, a squearyrium series pigment, or a perylene series pigment.

4. An image-forming process, which comprises uniformly negatively charging the surface of the electrophotographic photosensitive member described in claim 1, applying thereto electrophotographic exposing radiation to form electrostatic latent images, attaching negatively charged toners to exposed portions of the electrostatic latent images to form toner images, superposing a transfer material on the electrophotographic photosensitive member carrying the toner images, and applying to the photosensitive member a positive charge from the back surface of the transfer material to transfer the toner images onto the transfer material.

5. An image-forming process, which comprises uniformly negatively charging the surface of the electrophotographic photosensitive member described in claim 1, applying thereto a first exposing radiation to form first electrostatic latent images, attaching negatively charged toners to relatively discharged portions of the first electrostatic latent images to form first toner images, then, applying thereto a second exposing radiation to form second electrostatic latent images, attaching positively charged second toners to relatively undischarged portions of the second electrostatic latent images to form second toner images, after unifying the polarities of the first and second toner images to one of the polarities, superposing a transfer material on the electrophotographic photosensitive member carrying the first and second toner images, and applying a charge having the opposite polarity to the one polarity of the first and second toner images from the back surface of the transfer material to transfer the first and second toner images onto the transfer material.

6. The electrophotographic photosensitive member having a charge generating layer and a charge transporting layer successively formed on a support, as claimed in claim 1, wherein, in the charge generating layer, the at least one compound comprises a compound represented by the formula (Ia), said compound being produced by reacting an anthraquinone compound and malononitrile in the presence of TiCl$_4$.

7. The electrophotographic photosensitive member having a charge generating layer and a charge transporting layer successively formed on a support, as claimed in claim 1, wherein, in the charge generating layer, the at least one compound comprises a compound represented by the formula (Ic), said compound being produced by reacting an appropriate quinone compound and malononitrile in a solvent.

8. The electrophotographic photosensitive member having a charge generating layer and a charge transporting layer successively formed on a support, as claimed in claim 2, wherein, in the charge generating layer, the charge generating pigment having the hole transporting property is incorporated in said charge generating layer in a range from 0.1 to 10 parts by weight to one part by weight of the binder resin, said pigment being dispersed in said charge-generating layer as particles of said pigment of mean size not greater than 3 $\mu$m.

9. The electrophotographic photosensitive member having a charge generating layer and a charge transporting layer successively formed on a support, as claimed in claim 1, additionally including a protective layer formed over said successively formed layers.

10. The image-forming process of claim 5 in which the first and second toners have respectively different colors.

11. The image-forming process of claim 10 in which the second exposing radiation is substantially less intense than said first exposing radiation.

* * * * *

UNITED STATES PATENT AND TRADEMARK OFFICE
CERTIFICATE OF CORRECTION

PATENT NO. : 5,102,757
DATED : April 7, 1992
INVENTOR(S) : Yutaka Akasaki et al

It is certified that error appears in the above-indentified patent and that said Letters Patent is hereby corrected as shown below:

Title page, item [30] Priority Data, change "Oct. 15, 1988"

to --Oct. 5, 1988--

Column 56, line 46, claim 3, change "squearyrium" to

--squarylium--.

Signed and Sealed this

Seventh Day of December, 1993

*Attest:*

BRUCE LEHMAN

*Attesting Officer*  *Commissioner of Patents and Trademarks*